US005677184A

United States Patent [19]
Onda et al.

[11] Patent Number: 5,677,184
[45] Date of Patent: Oct. 14, 1997

[54] CHO CELLS THAT EXPRESS HUMAN LH-RH RECEPTOR

[75] Inventors: Haruo Onda; Shoichi Ohkubo; Shuji Hinuma, all of Ibaraki; Hidekazu Sawada, Osaka, all of Japan

[73] Assignee: Takeda Chemical Industries, Ltd., Osaka, Japan

[21] Appl. No.: 423,691

[22] Filed: Apr. 18, 1995

[30] Foreign Application Priority Data

Apr. 19, 1994 [JP] Japan ..................... 6-080731
Sep. 13, 1994 [JP] Japan ..................... 6-218349

[51] Int. Cl.⁶ ................................... C12N 15/85
[52] U.S. Cl. ............................. 435/360; 435/358
[58] Field of Search .................. 435/69.1, 240.2, 435/240.25, 240.31, 245, 252.3, 70.3, 358, 325, 360

[56] References Cited

U.S. PATENT DOCUMENTS 5,053,334  10/1991  Anathoon et al. ............... 435/226

FOREIGN PATENT DOCUMENTS 9400590  1/1994  WIPO .

OTHER PUBLICATIONS

Kakar et al. BBRC (1992) 189: 289–295.
Chi et al. Mol. Cell. Endocrinal. (1993) 91:1–6.
Yamauchi et al. Biosci. Biotech Biochem (1992) 56: 600–604.
Costagliola et al. J. Clin. Endocrin. Metab. (1992) 75:1540–1544.
Nagayama et al. Biochem. Biophys. Res. Comm. 165(1989) 1184–1190.

*Primary Examiner*—Marianne P. Allen
*Assistant Examiner*—Robert C. Hayes
*Attorney, Agent, or Firm*—David G. Conlin; David S. Resnick; Dike, Bronstein Roberts & Cushman, LLP

[57] ABSTRACT

Disclosed are CHO cells which are capable of continued production of human LH-RH receptor proteins, or cell membrane fractions thereof; recombinant human LH-RH receptor proteins or partial peptides thereof; methods for screening compounds which have affinity for an LH-RH receptor by contacting the compound with the CHO cells or the cell membrane fractions thereof, or the recombinant human LH-RH receptor proteins or the partial peptides thereof; kits for screening them; the compounds which have affinity for the LH-RH receptor obtained by methods for the screening or kits for the screening; and pharmaceutical compositions containing the compound, thereby being able to early provide prophylactic or therapeutic compositions, for example, for prostate cancer, uterine cancer, breast cancer, a pituitary tumor, endometriosis, hysteromyoma or precocious puberty. They are also useful as a pregnancy controlling composition such as contraceptive or a menstrual cycle controlling composition.

2 Claims, 4 Drawing Sheets

```
5'AAAATATCAG ATGCACCAGA GACACAAGGC TTGAAGCTCT GTCCTGGGAA AATATGGCAA      60
  ACAGTGCCTC TCCTGAACAG AATCAAAATC ACTGTTCAGC CATCAACAAC AGCATCCCAC     120
  TGATGCAGGG CAACCTCCCC ACTCTGACCT TGTCTGGAAA GATCCGAGTG ACGGTTACTT     180
  TCTTCCTTTT TCTGCTCTCT GCGACCTTTA ATGCTTCTTT CTTGTTGAAA CTTCAGAAGT     240
  GGACACAGAA GAAAGAGAAA GGGAAAAAGC TCTCAAGAAT GAAGCTGCTC TTAAAACATC     300
  TGACCTTAGC CAACCTGTTG GAGACTCTGA TTGTCATGCC ACTGGATGGG ATGTGGAACA     360
  TTACAGTCCA ATGGTATGCT GGAGAGTTAC TCTGCAAAGT TCTCAGTTAT CTAAAGCTTT     420
  TCTCCATGTA TGCCCCAGCC TTCATGATGG TGGTGATCAG CCTGGACCGC TCCCTGGCTA     480
  TCACGAGGCC CCTAGCTTTG AAAAGCAACA GCAAAGTCGG ACAGTCCATG GTTGGCCTGG     540
  CCTGGATCCT CAGTAGTGTC TTTGCAGGAC CACAGTTATA CATCTTCAGG ATGATTCATC     600
  TAGCAGACAG CTCTGGACAG ACAAAAGTTT TCTCTCAATG TGTAACACAC TGCAGTTTTT     660
  CACAATGGTG GCATCAAGCA TTTTATAACT TTTTCACCTT CAGCTGCCTC TTCATCATCC     720
  CTCTTTTCAT CATGCTGATC TGCAATGCAA AAATCATCTT CACCCTGACA CGGGTCCTTC     780
  ATCAGGACCC CCACGAACTA CAACTGAATC AGTCCAAGAA CAATATACCA AGAGCACGGC     840
  TGAAGACTCT AAAAATGACG GTTGCATTTG CCACTTCATT TACTGTCTGC TGGACTCCCT     900
  ACTATGTCCT AGGAATTTGG TATTGGTTTG ATCCTGAAAT GTTAAACAGG TTGTCAGACC     960
  CAGTAAATCA CTTCTTCTTT CTCTTTGCCT TTTTAAACCC ATGCTTTGAT CCACTTATCT    1020
  ATGGATATTT TTCTCTGTGA TTGATAGACT ACACAAGAAG TCATATGAAG AAGGGTAAGG    1080
  TAATGAATCT CTCCATCTGG GAATGATTAA CACAAATGTT GGAGCATGTT TACATACAAA    1140
  CAAAGTAGGA TTTACACTTA AGTTATCATT CTTTTAGAAA CTCAGTCTTC AGAGCCTCAA    1200
  TTATTAAGGA AAAGTCTTCA GGAAAAATAC TAAAATATTT TCTCTTCCTC ATAAGCTTCT    1260
  AAATTAATCT CTGCCTTTTC TGACCTCATA TAACACATTA TGTAGGTTTC TTATCACTTT    1320
  CTCTTTGCAT AATAATGTAC TAATATTTAA AATACCTTCA GCCTAAGGCA CAAGGATGCC    1380
  AAAAAAACAA AGGTGAGAAA CCACAACACA GGTCTAAACT CAGCATGCTT TGGTGAGTTT    1440
  TTCTCCAAAA GGGGCATATT AGCAATTAGA GTTGTATGCT ATATAATACA TAGAGCACAG    1500
  AGCCCTTTGC CCATAATATC AACTTTCCCT CCTATAGTTA AAAAAAAAAA AAA 3'        1553
```

FIG. 1

N-Met Ala Asn Ser Ala Ser Pro Glu Gln Asn Gln Asn His Cys Ser Ala
    1                                   10
    Ile Asn Asn Ser Ile Pro Leu Met Gln Gly Asn Leu Pro Thr Leu Thr
                 20                                   30
    Leu Ser Gly Lys Ile Arg Val Thr Val Thr Phe Phe Leu Phe Leu Leu
                                 40
    Ser Ala Thr Phe Asn Ala Ser Phe Leu Leu Lys Leu Gln Lys Trp Thr
        50                                       60
    Gln Lys Lys Glu Lys Gly Lys Lys Leu Ser Arg Met Lys Leu Leu Leu
                     70                                           80
    Lys His Leu Thr Leu Ala Asn Leu Leu Glu Thr Leu Ile Val Met Pro
                                         90
    Leu Asp Gly Met Trp Asn Ile Thr Val Gln Trp Tyr Ala Gly Glu Leu
                 100                                      110
    Leu Cys Lys Val Leu Ser Tyr Leu Lys Leu Phe Ser Met Tyr Ala Pro
                             120
    Ala Phe Met Met Val Val Ile Ser Leu Asp Arg Ser Leu Ala Ile Thr
        130                                      140
    Arg Pro Leu Ala Leu Lys Ser Asn Ser Lys Val Gly Gln Ser Met Val
                     150                                          160
    Gly Leu Ala Trp Ile Leu Ser Ser Val Phe Ala Gly Pro Gln Leu Tyr
                                     170
    Ile Phe Arg Met Ile His Leu Ala Asp Ser Ser Gly Gln Thr Lys Val
                 180                                      190
    Phe Ser Gln Cys Val Thr His Cys Ser Phe Ser Gln Trp Trp His Gln
                                 200
    Ala Phe Tyr Asn Phe Phe Thr Phe Ser Cys Leu Phe Ile Ile Pro Leu
        210                                      220
    Phe Ile Met Leu Ile Cys Asn Ala Lys Ile Ile Phe Thr Leu Thr Arg
                         230                                      240
    Val Leu His Gln Asp Pro His Glu Leu Gln Leu Asn Gln Ser Lys Asn
                                     250
    Asn Ile Pro Arg Ala Arg Leu Lys Thr Leu Lys Met Thr Val Ala Phe
                 260                                      270
    Ala Thr Ser Phe Thr Val Cys Trp Thr Pro Tyr Tyr Val Leu Gly Ile
                                 280
    Trp Tyr Trp Phe Asp Pro Glu Met Leu Asn Arg Leu Ser Asp Pro Val
        290                                      300
    Asn His Phe Phe Phe Leu Phe Ala Phe Leu Asn Pro Cys Phe Asp Pro
                             310                                  320
    Leu Ile Tyr Gly Tyr Phe Ser Leu * * * -C

F I G. 2

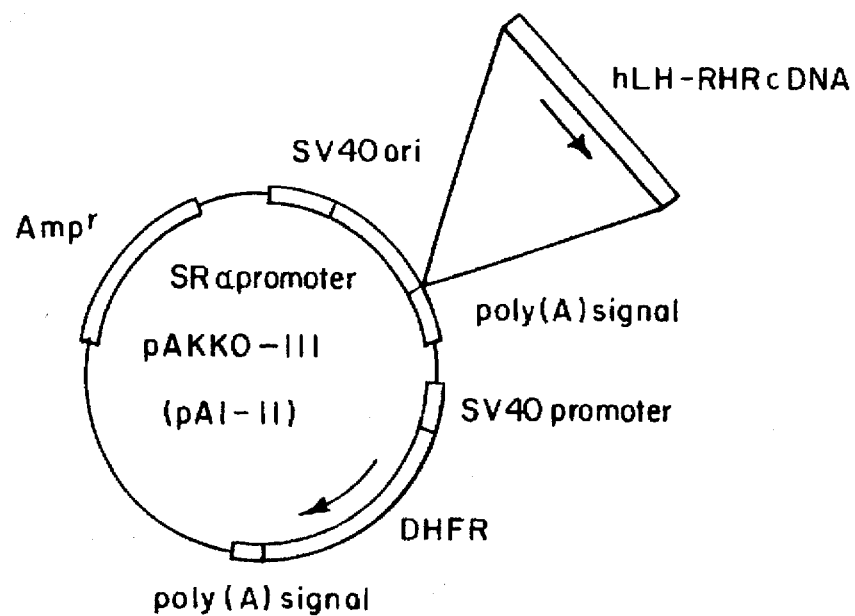
F I G. 3
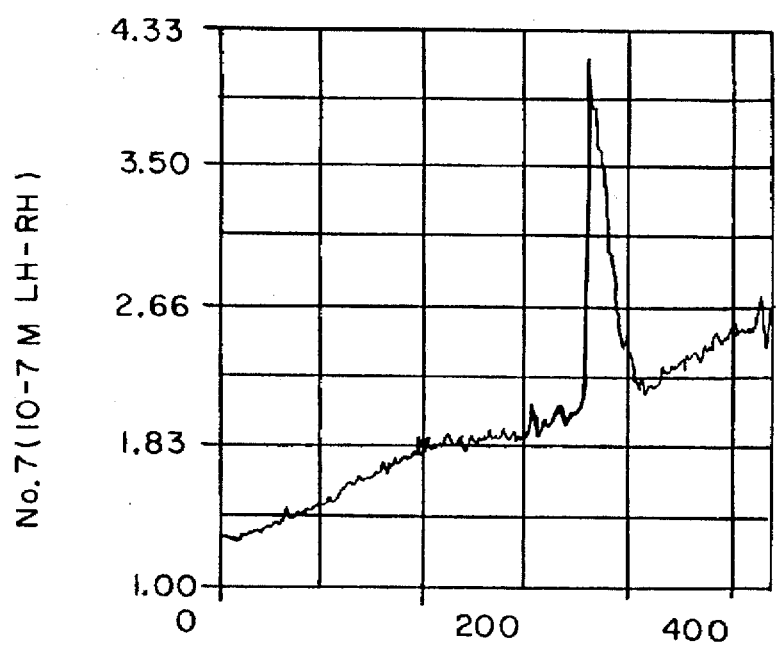
F I G. 4

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 984 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:1:

```
ATGGCAAACA GTGCCTCTCC TGAACAGAAT CAAAATCACT GTTCAGCCAT CAACAACAGC       60

ATCCCACTGA TGCAGGGCAA CCTCCCCACT CTGACCTTGT CTGGAAAGAT CCGAGTGACG      120

GTTACTTTCT TCCTTTTTCT GCTCTCTGCG ACCTTTAATG CTTCTTTCTT GTTGAAACTT      180

CAGAAGTGGA CACAGAAGAA AGAGAAAGGG AAAAAGCTCT CAAGAATGAA GCTGCTCTTA      240

AAACATCTGA CCTTAGCCAA CCTGTTGGAG ACTCTGATTG TCATGCCACT GGATGGGATG      300

TGGAACATTA CAGTCCAATG GTATGCTGGA GAGTTACTCT GCAAAGTTCT CAGTTATCTA      360

AAGCTTTTCT CCATGTATGC CCCAGCCTTC ATGATGGTGG TGATCAGCCT GGACCGCTCC      420

CTGGCTATCA CGAGGCCCCT AGCTTTGAAA AGCAACAGCA AAGTCGGACA GTCCATGGTT      480

GGCCTGGCCT GGATCCTCAG TAGTGTCTTT GCAGGACCAC AGTTATACAT CTTCAGGATG      540

ATTCATCTAG CAGACAGCTC TGGACAGACA AAAGTTTTCT CTCAATGTGT AACACACTGC      600

AGTTTTTCAC AATGGTGGCA TCAAGCATTT TATAACTTTT TCACCTTCAG CTGCCTCTTC      660

ATCATCCCTC TTTTCATCAT GCTGATCTGC AATGCAAAAA TCATCTTCAC CCTGACACGG      720

GTCCTTCATC AGGACCCCCA CGAACTACAA CTGAATCAGT CCAAGAACAA TATACCAAGA      780
```

```
GCACGGCTGA AGACTCTAAA AATGACGGTT GCATTTGCCA CTTCATTTAC TGTCTGCTGG        840
ACTCCCTACT ATGTCCTAGG AATTTGGTAT TGGTTTGATC CTGAAATGTT AAACAGGTTG        900
TCAGACCCAG TAAATCACTT CTTCTTTCTC TTTGCCTTTT TAAACCCATG CTTTGATCCA        960
CTTATCTATG GATATTTTTC TCTG                                                984
```

( 2 ) INFORMATION FOR SEQ ID NO:2:

( i ) SEQUENCE CHARACTERISTICS:
        ( A ) LENGTH: 328 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Asn Ser Ala Ser Pro Glu Gln Asn Gln Asn His Cys Ser Ala
 1               5                  10                  15

Ile Asn Asn Ser Ile Pro Leu Met Gln Gly Asn Leu Pro Thr Leu Thr
                20                  25                  30

Leu Ser Gly Lys Ile Arg Val Thr Val Thr Phe Phe Leu Phe Leu Leu
            35                  40                  45

Ser Ala Thr Phe Asn Ala Ser Phe Leu Leu Lys Leu Gln Lys Trp Thr
        50                  55                  60

Gln Lys Lys Glu Lys Gly Lys Lys Leu Ser Arg Met Lys Leu Leu Leu
65                  70                  75                  80

Lys His Leu Thr Leu Ala Asn Leu Leu Glu Thr Leu Ile Val Met Pro
                85                  90                  95

Leu Asp Gly Met Trp Asn Ile Thr Val Gln Trp Tyr Ala Gly Glu Leu
            100                 105                 110

Leu Cys Lys Val Leu Ser Tyr Leu Lys Leu Phe Ser Met Tyr Ala Pro
        115                 120                 125

Ala Phe Met Met Val Val Ile Ser Leu Asp Arg Ser Leu Ala Ile Thr
    130                 135                 140

Arg Pro Leu Ala Leu Lys Ser Asn Ser Lys Val Gly Gln Ser Met Val
145                 150                 155                 160

Gly Leu Ala Trp Ile Leu Ser Ser Val Phe Ala Gly Pro Gln Leu Tyr
                165                 170                 175

Ile Phe Arg Met Ile His Leu Ala Asp Ser Ser Gly Gln Thr Lys Val
            180                 185                 190

Phe Ser Gln Cys Val Thr His Cys Ser Phe Ser Gln Trp Trp His Gln
        195                 200                 205

Ala Phe Tyr Asn Phe Phe Thr Phe Ser Cys Leu Phe Ile Ile Pro Leu
    210                 215                 220

Phe Ile Met Leu Ile Cys Asn Ala Lys Ile Ile Phe Thr Leu Thr Arg
225                 230                 235                 240

Val Leu His Gln Asp Pro His Glu Leu Gln Leu Asn Gln Ser Lys Asn
                245                 250                 255

Asn Ile Pro Arg Ala Arg Leu Lys Thr Leu Lys Met Thr Val Ala Phe
            260                 265                 270

Ala Thr Ser Phe Thr Val Cys Trp Thr Pro Tyr Tyr Val Leu Gly Ile
        275                 280                 285

Trp Tyr Trp Phe Asp Pro Glu Met Leu Asn Arg Leu Ser Asp Pro Val
    290                 295                 300

Asn His Phe Phe Phe Leu Phe Ala Phe Leu Asn Pro Cys Phe Asp Pro
305                 310                 315                 320
```

Leu Ile Tyr Gly Tyr Phe Ser Leu
              325

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:3:

TGAAGCCTGT CCTTGGAGAA ATATGGC         27

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:4:

AAAGTTGTAG AAGGCCTGAT GCCACCA         27

(2) INFORMATION FOR SEQ ID NO:5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:5:

GACGGCCGCA GATCTCCATG GCAAACAGTG CCTCTCC         37

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:6:

GACAGATCTC ACAGAGAAAA ATATCCATAG         30

CHO CELLS THAT EXPRESS HUMAN LH-RH RECEPTOR

FIELD OF THE INVENTION

The present invention relates to Chinese Hamster Ovary (CHO) cells having ability to continue producing human LH-RH (luteinizing hormone-releasing) receptor proteins, or cell membrane fractions thereof; recombinant human LH-RH receptor proteins or peptide fragments thereof; methods for screening a compound or a salt thereof which has affinity for an LH-RH receptor by using the CHO cells or the cell membrane fractions thereof, or the recombinant human LH-RH receptor proteins or the peptide fragments thereof; kits for screening a compound or a salt thereof which has affinity for an LH-RH receptor; the compound or the salt thereof, which has affinity for an LH-RH receptor, obtained by the screening methods or the kits for screening; and pharmaceutical compositions containing the compound or the salt thereof.

BACKGROUND OF THE INVENTION

LH-RH (luteinizing hormone-releasing hormone) is a peptide consisting of 10 amino acids which was first isolated from the hypothalami of pigs (H. Matsuo et al., *Biochem. Biophys. Res. Commun.*, 43, 1334–1339 (1971)), and has activity to act on the anterior lobes of pituitaries to allow them to release gonadotropic hormones (LH and follicle stimulating hormone (FSH)) (R. N. Clayton et al., *Endocr. Rev.*, 2, 186–209 (1981)). Of the two kinds of gonadotropic hormones, both coexisting with each other induce secretion of estrogenic hormone for females, and LH alone induces secretion of androgenic hormone for males. As described above, LH-RH is a leading hormone playing an important role in the control of the gonadal and sex hormones, and has affects on the genital organs such as the gonad and the uterus. In particular, drugs for inhibiting the activity of LH-RH are known to stop the progress of prostatic cancer dependent on androgenic hormone. Further, similar drugs are also known to be effective against endometriosis due to heterotopic abnormal proliferation of endometrial tissue. However, since such drugs are peptides and oral administration thereof is impossible, injection thereof is necessary.

On the other hand, LH-RH receptors exist in LH secretory cells and FSH secretory cells of the anterior lobes of pituitaries, the stimulation of LH-RH is transmitted to these cells through LH-RH receptors. Further, the LH-RH receptors are also known to be expressed in the placenta (A. J. Currie et al., *Biochem. Biophys. Res. Commun.*, 99, 332–338 (1981), *Nature*, 282, 90–92 (1979), and R. N. Clayton et al., *Proc. Natl. Acad. Sci. USA*, (1980)), the adrenal medulla (D. R. Pieper et al., *Endocrinology*, 108, 1148–1155 (1981)), the brain (L. Jennes et al., *Brain Res.*, 452, 156–164 (1988)) and some kinds of tumors [M. A. Millan et al., *Methods Enzymol.*, 124, 590–606 (1986)] as well as in the pituitaries, and the development of drugs for enhancing or blocking the activity of LH-RH is considered to be effective against various diseases.

For example, leuprorelin acetate which is a highly active derivative of LH-RH (hereinafter referred to as an LH-RH receptor superagonistic compound) (Fujino et al., *Biochemical and Biophysical Research Communications*, 60, 406–413 (1974); R. T. D. Oliver et al., *Br. J. Cancer*, 59, 823 (1989); Toguchi et al., *J. Int. Med. Res.*, 18, 35–41 (1990)) reduces release and production of gonadotropic hormones in the pituitaries, induces a decrease in reactivity on gonadotropic hormones to the testes and the ovaries, and inhibits secretion of testosterone and estrogen by repeated administrations. As a result, leuprorelin acetate is known to exhibit antitumor activity on such hormone-dependent cancers such as prostate cancer, and thus has been clinically applied. Further, leuprorelin acetate is also widely clinically used as a therapeutic agent for endometriosis, precocious puberty, etc. The high anticancer activity of leuprorelin acetate is presumed to result from its resistance against proteases, compared with that of natural LH-RH, and high affinity for the LH-RH receptors, which causes desensitization.

However, leuprorelin acetate is the superagonistic compound to the LH-RH receptors, so that transient aggravation accompanied by an increase in serum testosterone concentration due to pituitary-gonadotropic action (acute action) is observed immediately after initial administration. Accordingly, a compound having no superagonistic action, that is an LH-RH receptor antagonistic compound, is expected as a better therapeutic agent for endometriosis, precocious puberty, etc., compared with the LH-RH receptor superagonistic compound.

In general, when a superagonist or an antagonist to a certain biologically active substance's receptor is developed, a compound which has high affinity for a receptor is screened. As the LH-RH receptors, bovine or rat pituitary membrane fractions are now used. However, it is not guaranteed that the screened compounds are effective in humans, because the LH-RH receptors are from different animal species. Human LH-RH receptor cDNA was cloned and the expression thereof in COS7 cells was also reported (S. S. Kakar et al., *Biochem. Biophys. Res. Commun.*, 189, 289–295 (1992)). However, the expression amount in COS7 cells is extremely small, and further the expression is transient. It is therefore considered that COS7 cells are unsuitable for screening use. Use of human pituitary fractions as human LH-RH receptor protein have been considered. However, human-derived tissues are very difficult to be obtained, resulting in unsuitableness for screening use.

So, it is desired to develop cells which express a large quantity of human LH-RH receptors in order to screen an LH-RH superagonist or an LH-RH antagonist effectively.

LH-RH is also called GnRH because LH-RH stimulates release of not only LH but also FSH after LH-RH binding to an LH-RH receptor. In the present specification, the term, "LH-RH", is employed.

SUMMARY OF THE INVENTION

An object of the present invention is to provide CHO cells having ability to express human LH-RH receptor, cell membrane fractions thereof; recombinant human LH-RH receptor proteins or peptide fragments thereof; methods for screening a compound or a salt thereof which has affinity for an LH-RH receptor by using the CHO cells or the cell membrane fractions thereof, or the recombinant human LH-RH receptor proteins or the peptide fragments thereof; kits for screening compounds or a salt thereof which has affinity for an LH-RH receptor. It is also an object of the present invention to use the disclosed screening methods to obtain compounds or a salt thereof which have affinity for an LH-RH receptor obtained by the screening methods or the kits for screening; and pharmaceutical compositions containing the compound or the salt thereof can then be prepared.

The present inventors have conducted intensive investigation on methods for screening compounds which have affinity for an LH-RH receptor and have succeeded in producing CHO cells which can express human LH-RH receptors at high efficiency.

The present invention provides:

(1) A CHO cell containing a DNA coding for a human LH-RH receptor protein, continuously expressing a recombinant human LH-RH receptor protein from said DNA, and wherein said cell is capable of continued production of a recombinant human LH-RH receptor protein having activities substantially equivalent to those of a natural human LH-RH receptor protein;

(2) A CHO cell containing a recombinant human LH-RH receptor protein, which is produced by cultivating the CHO cell described in (1) under conditions such that the recombinant human LH-RH receptor protein is continuously expressed from a DNA coding for a human LH-RH receptor protein, or a cell membrane fraction thereof;

(3) The CHO cell described in (1) or (2), which is a CHO cell capable of proliferation in suspension;

(4) A recombinant human LH-RH receptor protein, a peptide fragment thereof or a salt thereof having activities substantially equivalent to those of a natural human LH-RH receptor protein, which is isolated from the CHO cell described in (2);

(5) A method for producing a recombinant human LH-RH receptor protein, which comprises cultivating the CHO cell described in (1) under conditions suitable for expression of the recombinant human LH-RH receptor, continuously expressing a recombinant human LH-RH receptor protein from said DNA and wherein said cell is capable of continued production of a recombinant human LH-RH receptor protein having activities substantially equivalent to those of a natural human LH-RH receptor protein;

(6) The method described in (5), in which said CHO cell is a CHO cell capable of proliferation in suspension;

(7) A method for screening a compound or a salt thereof which has affinity for an LH-RH receptor, which comprises contacting the compound with the CHO cell or the cell membrane fraction thereof described in (2) and measuring the affinity of said compound for the LH-RH receptor;

(8) A method for screening a compound or a salt thereof which has affinity for an LH-RH receptor, which comprises contacting the compound with the recombinant human LH-RH receptor protein, the peptide fragment thereof or a salt thereof described in (4) and measuring the affinity of said compound for the LH-RH receptor;

(9) A kit for screening a compound or a salt thereof which has affinity for an LH-RH receptor, which contains the CHO cell or the cell membrane fraction thereof described in (2), or the recombinant human LH-RH receptor protein, the peptide fragment thereof or a salt thereof described in (4);

(10) A compound or a salt thereof which has affinity for an LH-RH receptor which is obtained by the method described in (7) or (8), or by use of the kit described in (9);

(11) The compound described in (10) which is an LH-RH receptor agonistic compound;

(12) The compound described in (10) which is an LH-RH receptor superagonistic compound;

(13) The compound described in (10) which is an LH-RH receptor antagonistic compound;

(14) A pharmaceutical composition comprising the compound of (11) and a pharmaceutically acceptable carrier;

(15) A pharmaceutical composition comprising the compound of (12) and a pharmaceutically acceptable carrier;

(16) A pharmaceutical composition comprising the compound of (13) and a pharmaceutically acceptable carrier;

(17) An animal pregnancy controlling composition or an animal menstrual cycle controlling composition which comprises an effective amount of the LH-RH receptor agonistic compound or a salt thereof described in (11);

(18) A prophylactic and/or therapeutic composition for prostate cancer, uterine cancer, breast cancer, a pituitary tumor, endometriosis, hysteromyoma or precocious puberty; or a pregnancy controlling composition or a menstrual cycle controlling composition, which comprises the LH-RH receptor superagonistic compound or a salt thereof described in (12); and

(19) A prophylactic and/or therapeutic composition for prostate cancer, uterine cancer, breast cancer, a pituitary tumor, endometriosis, hysteromyoma or precocious puberty; or a pregnancy controlling composition or a menstrual cycle controlling composition, which comprises the LH-RH receptor antagonistic compound or a salt thereof described in (13).

More specifically, the present invention provides:

(20) The CHO cell described in (1) or (2), which is a CHO cell designated CHO/L39, or a CHO cell designated CHO/L39-7 (FERM BP-4953);

(21) The CHO cell described in (3), in which the CHO cell capable of proliferation in suspension is a CHO cell designated CHO/LH-8 (FERM BP-4973) or a CHO cell designated CHO/LS;

(22) The CHO cell described in (1) or (2), in which the DNA coding for the human LH-RH receptor protein is a DNA containing a DNA fragment having a nucleotide sequence represented by SEQ ID NO: 1;

(23) The recombinant human LH-RH receptor protein, the peptide fragment thereof or a salt thereof described in (4), in which said recombinant human LH-RH receptor protein is a protein having an amino acid sequence represented by SEQ ID NO: 2, an amino acid sequence lacking one amino acid or two or more amino acids from the amino acid sequence represented by SEQ ID NO: 2, an amino acid sequence in which one amino acid or two or more amino acids are added to the amino acid sequence represented by SEQ ID NO: 2, or an amino acid sequence in which one amino acid or two or more amino acids in the amino acid sequence represented by SEQ ID NO: 2 are substituted by another amino acid or other amino acids, a protein in which an N-terminal signal peptide of said protein is removed, a protein in which a side chain of an amino acid in a molecule of said protein is protected with an appropriate protective group (for example, a $C_{1-6}$ acyl group such as formyl or acetyl), or a protein in which a sugar chain is bound to said protein;

(24) The method described in (7), which comprises comparing both following cases (i) and (ii), (i) contacting a ligand to an SH-RH receptor with the CHO cell or the cell membrane fraction thereof described in (2) and (ii) contacting a ligand to an LH-RH receptor and a test compound with the CHO cell or the cell membrane fraction thereof described in (2);

(25) The method described in (7), which comprises comparing the binding amounts of both following cases (i) and (ii), (i) contacting a labeled ligand to an LH-RH receptor with the CHO cell or the cell membrane fraction thereof described in (2) and (ii) contacting a labeled ligand to an LH-RH receptor and a test compound with the CHO cell or the cell membrane fraction thereof described in (2);

(26) A method for screening an LH-RH receptor agonistic compound or a salt thereof or an LH-RH receptor superagonistic compound or a salt thereof, which comprises contacting the CHO cell or the cell membrane fraction thereof described in (2) with a test compound; and measuring cell stimulation activities through the recombinant human LH-RH receptor (for example, activities enhancing or inhibiting arachidonic acid release, acetylcholine release, fluctuation in intracellular $Ca^{2+}$ concentration, generation of intracellular cAMP, generation of intracellular cGMP, production of inositol phosphate, fluctuation in cell membrane potential, phosphorylation of intracellular proteins, activation of c-fos, a reduction in pH, chemotactic activity, activation of guanine nucleotide refulatory proteins (G proteins) and cell growth);

(27) A method for screening an LH-RH receptor antagonistic compound or a salt thereof which comprises comparing the activities of both following cases (i) and (ii), (i) contacting the CHO cell or the cell membrane fraction thereof described in (2) with an LH-RH receptor agonist, and (ii) contacting the CHO cell or the cell membrane fraction thereof described in (2) with an LH-RH receptor agonist and a test compound, and in each case of (i) and (ii) measuring cell stimulation activities through the recombinant human LH-RH receptor (for example, activities enhancing or inhibiting arachidonic acid release, acetylcholine release, fluctuation in intracellular $Ca^{2+}$ concentration, generation of intracellular cAMP, generation of intracellular cGMP, production of inositol phosphate, fluctuation in cell membrane potential, phosphorylation of intracellular proteins, activation of c-fos, a reduction in pH, chemotactic activity, activation of guanine nucleotide regulatory proteins (G proteins) and cell growth);

(28) The method described in (8), which comprises comparing both following cases (i) and (ii), (i) contacting the recombinant human LH-RH receptor protein, a peptide fragment thereof or a salt thereof described in (4) with a ligand to an LH-RH receptor, and (ii) contacting the recombinant human LH-RH receptor protein, a peptide fragment thereof or a salt thereof described in (4) with a ligand to an LH-RH receptor and a test compound;

(29) The method described in (8), which comprises comparing the binding amounts of both following cases (i) and (ii), (i) contacting the recombinant human LH-RH receptor protein, a peptide fragment thereof or a salt thereof described in (4) with a labeled ligand to an LH-RH receptor, and (ii) contacting the recombinant human LH-RH receptor protein, a peptide fragment thereof or a salt thereof described in (4) with a labeled ligand to an LH-RH receptor and a test compound;

(30) A vector containing a DNA coding for a human LH-RH receptor protein which expresses a human LH-RH receptor protein, which is designated pA1-11/hLH-RHR contained in *Escherichia coli* MV1184//pA1-11/hLH-RHR (FERM BP-4645, IFO 15812);

(31) The CHO cell described in any one of (1)–(3) and (20)–(22), in which the DNA coding for the human LH-RH receptor protein is the expression vector described in (30);

(32) A method for producing the CHO cell capable of suspension culture described in (3) containing a DNA coding for a human LH-RH receptor protein, continuously expressing a recombinant human LH-RH receptor protein from said DNA and having ability to continue producing the recombinant human LH-RH receptor protein having activities substantially equivalent to those of a natural human LH-RH receptor protein, which comprises adapting the CHO cell described in (1) to an agitation culture in suspension by use of a serum-containing medium;

(33) A method for producing the CHO cell capable of suspension culture described in (3) containing a DNA coding for a human LH-RH receptor protein, continuously expressing a recombinant human LH-RH receptor protein from said DNA and having ability to continue producing the recombinant human LH-RH receptor protein having activities substantially equivalent to those of a natural human LH-RH receptor protein, which comprises adapting the CHO cell described in (1) to an agitation culture in suspension by use of a serum-containing medium, followed by adaptation to a serum-free medium;

(34) A method for producing the CHO cell capable of suspension culture described in (3) containing a DNA coding for a human LH-RH receptor protein, continuously expressing a recombinant human LH-RH receptor protein from said DNA and having ability to continue producing the recombinant human LH-RH receptor protein having activities substantially equivalent to those of a natural human LH-RH receptor protein, which comprises adapting the CHO cell described in (1) to a serum-free medium with a gradual decrease in serum concentration under an agitation culture in suspension;

(35) A method for producing the CHO cell capable of suspension culture described in (3) containing a DNA coding for a human LH-RH receptor protein, continuously expressing a recombinant human LH-RH receptor protein from said DNA and having ability to continue producing the recombinant human LH-RH receptor protein having activities substantially equivalent to those of a natural human LH-RH receptor protein, which comprises adapting the CHO cell described in (1) to a serum-free culture in static culture (for example, plate culture), followed by adapting to an agitation culture in suspension;

(36) A method for producing a cell capable of suspension culture containing a DNA coding for a human-derived receptor protein, constitutively expressing a recombinant receptor protein from said DNA and having ability to continue producing the recombinant receptor protein having activities substantially equivalent to those of a natural receptor protein, which comprises adapting a cell containing the DNA coding for the receptor protein, constitutively expressing a recombinant receptor protein from said DNA and wherein said cell is capable of continued production of the recombinant receptor protein having activities substantially equivalent to those of the natural receptor protein to an agitation culture in suspension by use of a serum-containing medium;

(37) A method for producing a cell capable of suspension culture containing a DNA coding for a human-derived receptor protein, constitutively expressing a recombinant receptor protein from said DNA and having ability to continue producing the recombinant receptor protein having activities substantially equivalent to those of a natural receptor protein, which comprises adapting a cell containing the DNA coding for the receptor protein, constitutively expressing a recombinant receptor protein from said DNA and having ability to continue producing the recombinant receptor protein having activities substantially equivalent to those of the natural receptor protein to an agitation culture in suspension by use of a serum-containing medium, followed by adapting to a serum-free medium, or

(38) A method for producing a cell capable of suspension culture containing a DNA coding for a human-derived receptor protein, constitutively expressing a recombinant receptor protein from said DNA and having ability to continue producing the recombinant receptor protein having activities substantially equivalent to those of a natural receptor protein, which comprises adaptating a cell containing the DNA coding for the human-derived receptor protein, constitutively expressing a recombinant receptor protein from said DNA and having ability to continue producing the recombinant human-derived receptor protein having activities substantially equivalent to those of the natural human-derived receptor protein to a serum-free medium with a gradual decrease in serum concentration under agitation culture in suspension;

(39) A method for producing a cell capable of suspension culture containing a DNA coding for a human-derived receptor protein, constitutively expressing a recombinant receptor protein from said DNA and having ability to continue producing the recombinant receptor protein having activities substantially equivalent to those of a natural receptor protein, which comprises adaptating a cell containing the DNA coding for the receptor protein, constitutively expressing a recombinant receptor from said DNA and having ability to continue producing the recombinant receptor protein having activities substantially equivalent to those of the natural receptor protein to a serum-free culture in static culture (for example, plate culture), followed by adaptating to an agitation culture in suspension; and

(40) A cell capable of proliferation in suspension produced by the method described in (36)-(39), which contains a DNA coding for a receptor protein, constitutively expresses a recombinant receptor protein from said DNA and has ability to keep producing a recombinant receptor protein having activities substantially equivalent to those of a natural receptor protein.

As used herein, the "recombinant human LH-RH receptor protein" is a protein, mutein or peptide fragment having biological activities substantially equivalent to those of the natural human LH-RH receptor protein. Substantially equivalence will depend on the particular activity one is looking at. Biological activities include, for example, ligand binding and signal information transmission, such as activities enhancing or inhibiting arachidonic acid release, acetylcholine release, fluctuation in intracellular $Ca^{2+}$ concentration, generation of intracellular cAMP, generation of intracellular cGMP, production of inositol phosphate, fluctuation in cell membrane potential, phosphorylation of intracellular proteins, activation of c-fos, a reduction in pH, chemotactic activity, activation of G proteins and cell growth.

BRIEF DESCRIPTION OF THE DRAWINGS

FIG. 1 shows a nucleotide sequence of cDNA coding for a human LH-RH receptor protein prepared in Reference Example 2;

FIG. 2 shows an amino acid sequence (SEQ ID NO:2) deduced from the nucleotide sequence shown in FIG. 1;

FIG. 3 is a schematic representation showing the construction of a human LH-RH receptor protein expression vector designated pA1-11/hLH-RHR, wherein $Amp^r$ represents an ampicillin resistant gene, DHFR represents a dihydrofolate reductase gene, and SV40ori represents an SV40 replicating origin;

FIG. 4 is a graph showing changes in intracellular calcium concentration on stimulation of a CHO/L39-7 cell by LH-RH, wherein the numbers on the ordinate indicate the ratio of fluorescences at 340 nm and 380 nm which shows the intracellular calcium concentration, and the numbers on the abscissa indicate elution time(unit: second);

DESCRIPTION OF THE PREFERRED EMBODIMENTS

Figure 5:
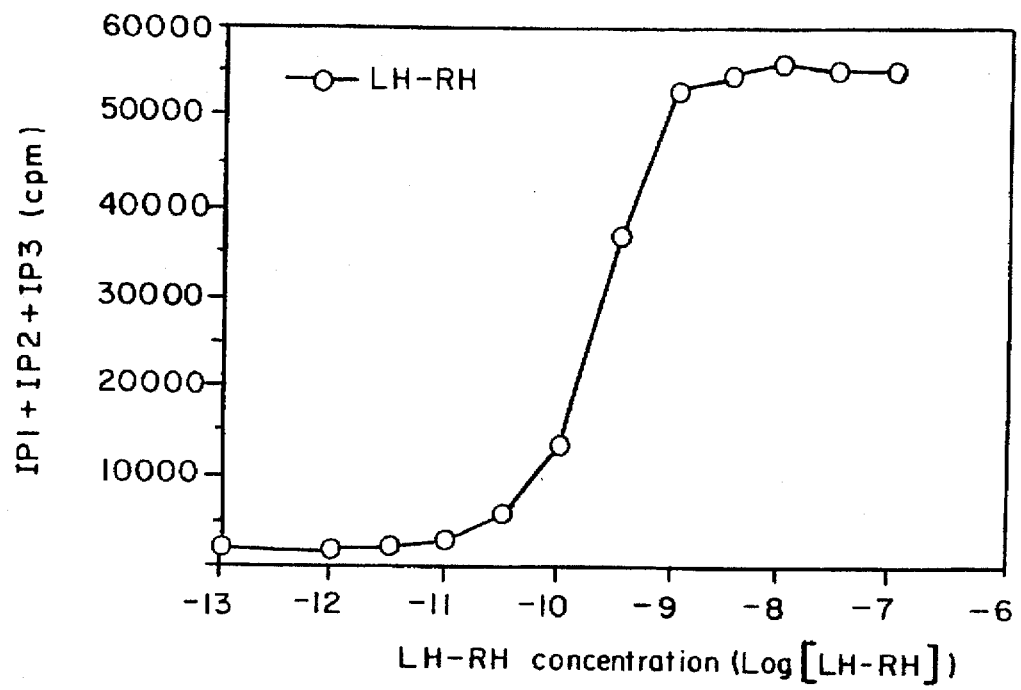
FIG. 5 is a graph showing changes in intracellular inositol phosphate concentration on stimulation of a CHO/L39-7 cell by LH-RH, wherein the numbers on the ordinate indicate the intracellular inositol phosphate concentration (cpm), and the numbers on the abscissa indicate the LH-RH concentration (log(LH-RH))

The CHO cell of the present invention containing the DNA coding for the human LH-RH receptor protein, constitutively expressing a recombinant human LH-RH receptor protein from said DNA, wherein said cell is capable of continued production of the recombinant human LH-RH receptor protein having activities substantially equivalent to those of the natural human LH-RH receptor protein is the CHO cell into which the expression vector containing the DNA coding for the human LH-RH receptor protein is introduced.

As the DNA coding for the human LH-RH receptor protein, for example, cDNA or genomic DNA coding for the human LH-RH receptor protein is used. However, it is not necessarily limited thereto as long as it has a nucleotide sequence coding for the human LH-RH receptor protein or a peptide fragment thereof having ligand binding activities substantially equivalent to those of the human LH-RH receptor protein. For example, although known cDNA or genomic DNA coding for the human LH-RH receptor protein can be used, synthetic DNA may also be used. Examples thereof include DNA having the nucleotide sequence represented by SEQ ID NO: 1 (the nucleotide sequence consisting of the 54th to 1037th nucleotides of the nucleotide sequence shown in FIG. 1) coding for a human LH-RH receptor protein having the amino acid sequence represented by SEQ ID NO: 2 (FIG. 2). Specifically, cDNA having the nucleotide sequence of FIG. 1 can be used. These DNAs can be cloned by genetic engineering techniques well known in the art, or can also be produced by use of a nucleotide synthesizer. For example, they can also be cloned according to the method described in Reference Example 2 given below or methods based thereon.

In order to introduce the DNA fragment coding for the human LH-RH receptor protein into the CHO cell to express the recombinant human LH-RH receptor protein, it is necessary to construct the expression vector.

The vectors include, for example, pA1-11, pXT1, pRc/CMV, pRc/RSV and pcDNAINeo. Any promoter is available as long as it effectively promotes expression in a host cell. Examples of the promoters include an SRα promoter, an SV40 promoter, an LTR promoter, a CMV promoter and an HSV-TK promoter. Of these, the CMV promoter and the SRα promoter are preferably used.

In addition to the above-mentioned promoters, the expression vectors may contain enhancers, splicing signals, polyadenylation signals, selection markers and SV40 replicating origin (hereinafter occasionally referred to as SV40ori) as so desired. The selection markers include, for example, dihydrofolate reductase thereinafter occasionally referred to as "DHFR" or "dhfr") genes[methotrexate (MTX) resistant], ampicillin resistant genes (hereinafter occasionally referred to as "Amp$^r$") and neomycin resistant genes (hereinafter occasionally referred to as "Neo$^r$", G418 resistance). In particular, when CHO(dhfr$^-$) cells are used and DHFR genes are used as the selection marker, selection can also be conducted on thymidine-free media.

Examples of the expression vectors each containing the DNA coding for the human LH-RH receptor include the above described vector such as pA1-11 into which the above-mentioned promoter (particularly, the SRα promoter) is inserted upstream from the DNA coding for the human LH-RH receptor protein, the polyadenylation signal is inserted downstream from the DNA coding for the human LH-RH receptor protein, further, the above-mentioned promoter (particularly, the SV40 promoter), the DHFR gene and/or the polyadenylation signal is inserted downstream therefrom, and preferably, the ampicillin resistant gene is further inserted downstream therefrom.

Specifically, the expression vector represented by pA1-11/hLH-RHR (FIG. 3) is preferred in which the SV40ori and SRα promoters are inserted upstream from the DNA coding for the human LH-RH receptor protein in vector pA1-11, the polyadenylation signal is inserted downstream from the DNA coding for the human LH-RH receptor protein, further, the SV40 promoter, the DHFR gene and the polyadenylation signal in this order are inserted downstream therefrom, and the ampicillin resistant gene is further inserted downstream therefrom.

Of the CHO cells (J. Exp. Med. 108, 945 (1958)), a CHO cell lacking the DHFR gene (Urlaub, G. et al. Proc. Natl. Acad. Sci. USA 77, 4216–4220 (1980)) (hereinafter briefly referred to as a "CHO(dhfr$^-$) cell" and CHO-K1 (Proc. Natl. Acad. Sci. USA 60, 1275 (1968)) are preferred, and the CHO(dhfr$^-$) cell is particularly preferred.

As to combinations of the expression vectors and host cells, preferred combinations can be appropriately selected. For example, the CHO(dhfr$^-$) cell is preferred as the host cell for the expression vector designated pA1-11/hLH-RHR (FIG. 3).

Even when the CHO(dhfr$^-$) cell is used as the host, if the DHFR gene has been inserted into the expression vector, the resulting CHO(dhfr$^-$) cell will have the DHFR gene. In this specification, the CHO cell obtained by introducing the DHFR gene-containing expression vector into the CHO (dhfr$^-$) cell is referred to as a "CHO(dhfr$^+$) cell" in some cases.

The human LH-RH receptor expression vectors thus prepared are introduced into the CHO cells by known methods. Such methods include, for example, the calcium phosphate method (F. L. Graham and A. J. van der Eb, *Virology*, 52, 456–467 (1973)) and electropotation method (E. Nuemann et al., *EMBO J.*, 1, 841–845 (1982)). As described above, CHO cells containing the human LH-RH receptor expression vectors are obtained.

Further, animal cells other than the CHO cells can also be used. The animal cells may be any as long as they can express the human LH-RH receptor proteins. Examples thereof include 293 cells, Vero cells, L cells, myeloma cells, C127 cells, BALB3T3 cells and Sp-2/0 cells. Of these, the 293 cell is preferred.

The CHO cell containing the recombinant human LH-RH receptor protein of the present invention can be produced by cultivating the CHO cell containing the DNA coding for the human LH-RH receptor-protein, constitutively expressing a recombinant human LH-RH receptor protein from said DNA, wherein said cell is capable of continued production of the recombinant human LH-RH receptor protein having activities substantially equivalent to those of the natural human LH-RH receptor protein, under such conditions that the DNA coding for the human LH-RH receptor protein can be constitutively expressed.

Methods for stably expressing the human LH-RH receptor proteins using the CHO cells described above include methods of selecting the CHO cells by clone selection in which the above-mentioned expression vectors are introduced into chromosomes. Specifically, transformants are selected based on the above-mentioned selection markers.

Further, repeated clone selections on the transformants thus obtained by using the selection markers make it possible to obtain stable cell lines having high expression of the human LH-RH receptor proteins. Furthermore, when the DHFR genes are used as the selection marker, cultivation can also be performed with a gradual increase in the concentration of MTX to select resistant cells, thereby amplifying the introduced genes in the cells to obtain higher expression CHO cell lines.

Media used in cultivating the above-mentioned CHO cells include EMEM medium supplemented with about 0.5 to 20% fetal calf serum, DMEM medium and RPMI1640 medium. In particular, when the CHO(dhfr$^-$) cell and the DHFR selection marker gene are used, DMEM medium containing thymidine-free dialyzed fetal calf serum is preferably used. The pH is desirably about 6 to 8. The cultivation is usually carried out at about 30° to 40° C. for about 15 to 72 hours with aeration and/or stirring if necessary.

Further, it is also effective to adaptate the CHO cell lines thus obtained to CHO cell lines capable of proliferation in suspension.

Namely, the present invention provides a method for producing a CHO cell capable of proliferation in suspension containing a DNA coding for a human LH-RH receptor protein, constitutively expressing a recombinant human LH-RH receptor protein from said DNA, wherein said cell is capable of continued production of the recombinant human LH-RH receptor protein having activities substantially equivalent to those of a natural human LH-RH receptor protein, which comprises (1) adaptating a CHO cell of the present invention containing the DNA coding for the human LH-RH receptor protein, constitutively expressing a recombinant human LH-RH receptor protein from said DNA and having ability to continue producing the recombinant human LH-RH receptor protein having activities substantially equivalent to those of the natural human LH-RH receptor protein to an agitation culture in suspension by use of a serum-containing medium, or (2) adaptating a CHO cell of the present invention containing the DNA coding for the human LH-RH receptor protein, constitutively expressing a recombinant human LH-RH receptor protein from said DNA and having ability to continue producing the recombinant human LH-RH receptor protein having activities substantially equivalent to those of the natural human LH-RH receptor protein to an agitation culture in suspension by use of a serum-containing medium, followed by adaptating to a serum-free medium, or (3) adaptating a CHO cell of the present invention containing the DNA coding for the human LH-RH receptor protein, constitutively expressing a recombinant human LH-RH receptor protein from said DNA and having ability to continue producing the recombinant human LH-RH receptor protein having activities substantially equivalent to those of the natural human LH-RH receptor protein to a serum-free medium with a gradual decrease in serum concentration under an agitation culture in suspension, or (4) adaptating a CHO cell of the present invention containing the DNA coding for the human LH-RH receptor protein, constitutively expressing a recombinant human LH-RH receptor protein from said DNA and having ability to continue producing the recombinant human LH-RH receptor protein having activities substantially equivalent to those of the natural human LH-RH receptor protein to a serum-free culture in static culture (for example, plate culture), followed by adaptating to an agitation culture in suspension.

The CHO cells are usually adaptated to agitation cultures in suspension by use of serum-containing media. Furthermore, it is also effective to adaptate the CHO cells to agitation cultures in suspension by use of serum-containing media, followed by adaptating to serum-free media. In addition, the serum concentration can be gradually decreased under agitation cultures in suspension to adaptate the CHO cells to serum-free media. Conversely, it is also useful to first adaptate the CHO cells to serum-free media by stationary cultures, followed by adaptating to agitation cultures in suspension.

When the CHO cells are adaptated to the agitation cultures in suspension by use of the serum-containing media, basal media usually employed for cultivation of the CHO cells into which appropriate serum such as fetal calf serum (FCS) is added in an amount of about 0.1 to 10%, preferably about 0.5 to 5%, to, or media containing serum-derived growth factor fractions (GFS) as serum substitutes (Tsukamoto et al., *Text for Second Symposium on Research and Development Project of Basic Technology for Future Industries*, 175 (1984)) are used.

Examples of the basal media include Eagle's MEM medium, Dulbecco's modified Eagle's medium (DMEM), Iscove medium (N. Iscove and F. Melchers, *J. Exp. Med.*, 147, 923 (1978)), Ham F12 medium (R. G. Ham, *Peoc. Nat. Acad. Sci.*, 53, 288 (1965)), L-15 medium (A. Leibovitz, *Amer. J. Hyg.*, 78, 173 (1963)), RPMI 1640 medium (G. E. Moore et al., *J. Amer. Med. Assoc.*, 199, 519 (1967)), ASF104 medium (Ajinomoto), CHSF medium (Gibco), COSMEDIUM-001 medium (Cosmobio), E-RDF medium (Kyokuto Seiyaku), UC-103 medium (Nissui Seiyaku), UC-202 medium (Nissui Seiyaku), S-Clone SF-02 medium (Sanko Junyaku), T medium (Nippon Seiyaku, Japanese. Patent Unexamined Publication (Laid-open) No. 60-145088), TL-2 medium (Y. Shintani et al., *Appl. Microbiol. Biotechnol.*, 27, 533 (1988)) and media in which they are mixed at appropriate ratios. Of these, ASF104 medium, E-RDF medium, TE medium and mixed media thereof are preferably used.

In adaptating to the serum-free media, the above-mentioned various basal media are used from which sera and serum substitutes are removed and to which amino acids, vitamins, nucleic acids, growth factors, hormones and other low molecular weight compounds are added alone or in appropriate combinations at appropriate concentrations. Specifically, media containing insulin, transferrin, ethanolamine, selenium, proline, polyethylene glycol (PEG), etc. are used. Furthermore, according to the selection markers used for transformation in introducing the genes, selection drugs such as methotrexate (MTX), mycophenolic acid and G418 may be added.

The serum concentration is gradually lowered to 0%, for example, by decreasing the serum concentration from about 5% to about 1%, from about 1% to about 0.1%, from about 0.1% to about 0.03% and from about 0.03% to 0% for every subculture of cells, and grown cells are recovered.

Any culture apparatus can be used for adaptation to agitation culture in suspension, as long as it is a small-sized reactor equipped with a stirring means. Examples thereof include spinner flasks, Techne spinner flasks, Erlenmeyer flasks and jar fermentors of various volumes.

Culture for cell adaptation to agitation culture in suspension and serum-free medium can be conducted according to known methods. For example, the subculture may be repeated at about 30° to 40° C. at an agitation speed of about 20 to 100 rpm for every about 3 to 7 days with pH adjustment and aeration if necessary. The total period required for such adaptation is about 1 to 5 months. The basal media may be appropriately changed in the course of the adaptation. This can expectedly give some allowance to growth adaptability of the resulting adapted cells to the basal media. The adapted cells of the present invention thus obtained substantially lose inherent adhesiveness and serum dependency, so that they exhibit no adhesiveness at all under such normal conditions as described above and are sufficiently viable under general agitation culture conditions.

It is also effective to use highly-productive clones selected from the adapted cell lines obtained in the manner as described above. The highly-productive clones can be selected according to methods well known in the art. Examples of the cloning methods include colony isolation, limiting dilution and the microwell method (*Shin Seikagaku Jikken Koza* (*Course of Biochemical Experiments, New Series*), 18, edited by Nippon Seikagaku Kai, *Cell Culture Techniques*, pages 12–13, Tokyo Kagaku Dojin (1990)). Further, it is of course preferred to repeat selections of the highly-productive clones using limiting dilution method, to subculture the cells with a gradual increase in the concentration of the selection drugs such as MTX to make them selection drug-resistant, thereby amplifying the structural genes of the human LH-RH receptor proteins, or to improve productivity at the line level by combining them.

Using the thus-obtained highly-productive CHO cell lines for the human LH-RH receptor proteins, large-scale cultivation is conducted to produce the target human LH-RH receptor proteins in large amounts. Culture apparatuses used in this case include known agitation culture tanks equipped with elements necessary for cultivation such as aeration means, agitation means, temperature control means, pH controlling means and dissolved oxygen (DO) adjusting means as so desired (*Shin Seikagaku Jikken Koza* (*Course of Biochemical Experiments, New Series*), 1, edited by Nippon Seikagaku Kai, *Proteins VI, Synthesis and Expression*, pages 282 and 286, Tokyo Kagaku Dojin (1992); *Shin Seikagaku Jikken Koza* (*Course of Biochemical Experiments, New Series*), 18, edited by Nippon Seikagaku Kai, *Cell Culture Techniques*, pages 12–13, Tokyo Kagaku Dojin (1990)).

Further, an air lift type fermentor (J. R. Birch et al., *Trends in Biotechnol.*, 3, 162 (1985)) is also used. Examples of cultivating methods include batch culture, feed culture (fed-batch culture) and perfusion culture. In order to conduct effective cultivation, perfusion culture in suspension is advantageous among others. In this cultivation, a fresh medium is supplied constitutively or intermittently, and the same amount of a culture supernatant is harvested constitutively or intermittently, whereby it becomes possible to maintain cells at high density in viable state for a long period of time.

In order to conduct perfusion culture, the culture vessel is equipped with a means for separating the cells in a culture broth from the culture supernatant, a means for discharging the culture supernatant, and a means for supplying the fresh medium. Examples of the means for separating the cells in the culture broth from the culture supernatant include filters, cone type cell sedimentation column and gravity sedimentation column utilizing cell sedimentation, and centrifugal separating means. For example, a method is preferably used in which the culture supernatant is constitutively discharged to changed with the fresh medium, using a culture system comprising the culture vessel equipped with such a separating means. The discharge of the culture supernatant and the supply of the fresh medium, or medium change, is performed during the period from the normal logarithmic growth phase to the stationary phase, from about 2 to 10 days, preferably about 3 to 7 days after initiation of normal cultivation, and it is preferred that the changing speed of the medium is gradually increased with an increase in cell density. Specifically, about 10 to 100%, preferably about 20 to 60%, of the culture liquid amount per day is changed.

For the media used for perfusion culture in suspension, media for cultivating CHO cells are appropriately prepared depending on the cells to be used, and usually, sera or serum substitutes (such as serum fractions) are added, or appropriate additives are added in place of them. Specifically, media are used in which sera or serum substitutes (such as serum fractions), insulin, transfertin, ethanolamine, selenium, proline, polyethylene glycol, etc. are added to the above-mentioned various basal media, preferably to ASF104 medium (Ajinomoto), E-RDF medium (Kyokuto Seiyaku), T medium (Nippon Seiyaku), TL-2 medium, TE medium (a 1:1:2 mixture of Iscove medium, Ham F12 medium and E-RDF medium), etc. Further, the selection drugs for gene-introduced cells such as MTX, mycophenolic acid and G418 are added if necessary. Specifically, PEG-86-1 medium (Shintani et al., *Appl. Microbiol. Biotechnol.*, 27, 533 (1988)) and PEG-TE medium (TE medium supplemented with 3.5 mg/l of insulin, 6.0 mg/l of transfertin, $2.5 \times 10^{-5}$ M of ethanolamine, $2.5 \times 10^{-8}$ M of selenious acid, 35 mg/l of proline, 10 µM of MTX and 1 g/l of PEG) are used.

In the agitation culture in suspension, the temperature is usually controlled to about 30° to 40° C., and preferably to about 37° C., the agitation speed to about 20 to 100 rpm, preferably to about 30 rpm, the pH to about 6 to 8, and preferably to about 7, and the DO to about 0.5 to 5 ppm, and preferably to about 1.5 ppm.

The cell containing the recombinant human LH-RH receptor protein can be produced from the cell containing the expression vector bearing the DNA coding for the human LH-RH receptor protein in the manner as described above.

Examples of the cells which can highly express the DNAs coding for the human LH-RH receptor proteins in the present invention include the CHO(dhfr⁻) cell containing the expression vector designated pA1-11/hLH-RHR which is obtained in Example 1 given below. Examples thereof include the CHO(dhfr⁺) cells designated CHO/L39 and CHO/L39-7. Of these, the CHO(dhfr⁺) cell designated CHO/L39-7 is preferred. Further, examples of the cells which can highly express the DNAs coding for the human LH-RH receptor proteins and can be suspension cultivated include CHO(dhfr⁺) cells designated CHO/LS and CHO/LH-8. Of these, the CHO(dhfr⁺) cell designated CHO/LH-8 is preferred.

These CHO(dhfr⁻) cells have receptor activities (for example, ligand binding activity) about 10 times higher than the recombinant human LH-RH receptor protein-containing COS-7 cells. Expression of receptor in COS-7 cells is transient but expression of receptor in CHO cells is continuous. Accordingly, the CHO cell which expresses the human LH-RH receptor of the present invention is useful for screening a compound or a salt thereof which has affinity for an LH-RH receptor.

Further, the above-mentioned methods for producing the CHO cells capable of proliferation in suspension can be applied not only to the human LH-RH receptor proteins, but also to all receptor proteins, and can be applied not only to the CHO cells, but also to all cells.

Namely, the present invention provides:

(1) a method for producing a cell capable of proliferation in suspension containing a DNA coding for a human-derived receptor protein, constitutively expressing a recombinant receptor protein from said DNA and having ability to continue producing a recombinant receptor protein having activities substantially equivalent to those of a natural receptor protein, which comprises (i) adaptating a cell containing the DNA coding for the human-derived receptor protein, constitutively expressing a recombinant receptor protein from said DNA and having ability to continue producing the recombinant human-derived receptor protein having activities substantially equivalent to those of the natural human-derived receptor protein to an agitation culture in suspension by use of a serum-containing medium, or (ii) adaptating a cell containing the DNA coding for the receptor protein, constitutively expressing a recombinant receptor protein from said DNA and having ability to continue producing the recombinant human-derived receptor protein having activities substantially equivalent to those of the natural receptor protein to an agitation culture in suspension by use of a serum-containing medium, followed by adaptating to a serum-free medium, or (iii) adaptating a cell containing the DNA coding for the human-derived receptor protein, constitutively expressing a recombinant receptor protein from said DNA and having ability to continue producing the recombinant receptor protein having activities substantially equivalent to those of the natural receptor protein to a serum-free medium with a gradual decrease in serum concentration under an agitation culture in suspension, or (iv) adaptating a cell containing the DNA coding for the receptor protein, constitutively expressing a recombinant receptor protein from said DNA and having ability to continue producing the recombinant receptor protein having activities substantially equivalent to those of the natural receptor protein to a serum-free culture in static culture (for example, plate culture), followed by adaptating to an agitation culture in suspension; and (2) a cell capable of proliferation in suspension produced by the method described in (1), which contains a DNA coding for a receptor protein, constitutively expresses a recombinant receptor protein from said DNA and has ability to continue producing the recombinant receptor protein having activities substantially equivalent to those of a natural receptor protein.

The receptor proteins are not limited to the human LH-RH receptor proteins. They may be either known or novel receptor proteins. Examples thereof include endothelin receptor proteins, TRH receptor proteins, PACAP receptor proteins, histamine receptor proteins, somatostatin receptor proteins, CRF receptor proteins, neurotensin receptor proteins, IL-8 receptor proteins, galanin receptor proteins, GHRH receptor proteins, prostaglandin $E_2$ receptor proteins, prostaglandin $I_2$ receptor proteins, bradykinin receptor proteins, CNP receptor proteins, CC chemokine receptor proteins, angiotensin receptor proteins, bombesin receptor proteins, kanabinoid receptor proteins, cholecystokinin receptor proteins, glutamine receptor proteins, serotonin receptor proteins, melatonin receptor proteins, neuropeptide Y receptor proteins, opioid receptor proteins, purine receptor proteins, vasopressin receptor proteins, oxytocin receptor proteins, VIP (Vasoactive intestinal and related peptide) receptor proteins, dopamine receptor proteins, motilin receptor proteins, amylin receptor proteins, bradykinin receptor proteins, CGRP (calcitonin gene related peptide) receptor proteins, leukotriene receptor proteins, pancreastatin receptor proteins, thromboxane receptor proteins, adenosine receptor proteins, adrenalin receptor proteins, GRO$\alpha$ receptor proteins, GRO$\beta$ receptor proteins, GRO$\gamma$ receptor proteins, NAP-2 receptor proteins, ENA-78 receptor proteins, PF-4 receptor proteins, IP10 receptor proteins, GCP-2 receptor proteins, MCP-1 receptor proteins, HC14 receptor proteins, MCP-3 receptor proteins, I-309 receptor proteins, MIP1$\alpha$ receptor proteins, MIP-1$\beta$ receptor proteins, RANTES receptor proteins, enterogastrine receptor proteins, pancreatic polypeptide receptor proteins and adrenomedulin receptor proteins.

The DNAs coding for these receptor proteins can be cloned by methods well known in the art or methods based thereon. Expression vectors containing the DNAs can be constructed by methods well known in the art or methods based thereon, specifically according to methods for constructing expression vectors containing the DNAs expressing the above-mentioned human LH-RH receptor proteins.

The cells capable of proliferation in suspension are not limited to the CHO cells. Any cells may be used as long as they can express the DNAs coding for the receptor proteins (preferably, human-derived receptor proteins) and can produce the recombinant receptor proteins having activities substantially equivalent to those of the natural receptor proteins. For example, they include Escherichia, Bacillus, yeast, insects and animal cells.

Examples of the Escherichia include *E. coli* K12·DH1 (*Proc. Natl. Acad. Sci. U.S.A.*, 60, 160 (1968)), JM103 (*Nucleic Acids Research*, 9, 309 (981)), JA221 (*Journal of Molecular Biology*, 120, 517 (1978)), HB101 (*Journal of Molecular Biology*, 41, 459 (1969)) and C600 (*Genetics*, 39, 440 (1954)).

Examples of the Bacillus include *Bacillus subtilis* MI114 (*Gene*, 24, 255 (1983)) and 207-21 (*Journal of Biochemistry*, 95, 87 (1984)).

Examples of the yeast include *Saccharomyces cerevisiae* AH22, AH22R⁻, NA87-11A, DKD-5D and 20B-12.

Examples of the insects include larvae of silk worms (Maeda et al., *Nature*, 315, 592 (1985)).

Examples of the animal cells include monkey cell COS-7, Vero cell, Chinese hamster cell (CHO), dhfr gene-lacking Chinese hamster cell CHO (CHO(dhfr⁻) cell), human FL cell, 293 cell, L cell, myeloma cell, C127 cell, Balb/c3T3 cell and Sp-2/O cell.

As to methods for introducing the expression vectors into the above-mentioned cells, methods for producing the cells capable of proliferation in suspension, methods for cultivating the cells capable of proliferation in suspension and methods for isolating the recombinant receptor proteins produced, methods similar to those used for the above-mentioned human LH-RH receptor proteins can be employed.

The cell membrane fraction of the cell (for example, the CHO cell) containing the recombinant human LH-RH receptor protein of the present invention means a fraction rich in the cell membrane content which is obtained by methods well known in the art after disruption of the cell containing the recombinant human LH-RH receptor protein of the present invention. Methods for disrupting the cell include crushing of the cell with a homogenizer and disruption with a Polytron or by sonication. For fractionation of the cell membrane, fractionation by centrifugal force such as differential centrifugation or density gradient centrifugation is mainly used. For example, a cell disrupted solution is centrifuged at a low speed (500 to 3,000 rpm) for a short period of time (1 to 10 minutes). Then, a supernatant is centrifuged at a high speed (15,000 to 40,000 rpm) for 30 to 120 minutes, and the resulting precipitate is used as a membrane fraction. The membrane fraction contains a large amount of membrane components such as the human LH-RH receptor protein, cell-derived phospholipids and membrane proteins.

The cells or the cell membrane fractions thereof thus obtained can be used for screening of the compounds which have affinity for the LH-RH receptors.

The amount of the human LH-RH receptor proteins in the cells containing the recombinant human LH-RH receptor proteins of the present invention or the cell membrane fractions thereof is preferably about 0.01 to about 100 pmol per 1 mg of the membrane protein, or preferably $10^3$ to $10^8$ molecules per cell, and more preferably $10^4$ to $10^6$ molecules per cell. The larger expression amount results in higher ligand binding activity (specific activity) per membrane fraction, and not only the construction of a highly sensitive screening system becomes possible, but also it becomes possible to measure a large amount of a sample of the same lot.

Examples of the recombinant human LH-RH receptor proteins of the present invention include the recombinant human LH-RH receptor protein having the amino acid sequence represented by SEQ ID NO: 2 which is produced by expressing the DNA having the nucleotide sequence represented by SEQ ID NO: 1. They further include the protein having the amino acid sequence lacking one amino acid or two or more amino acids in the amino acid sequence represented by SEQ ID NO: 2, the protein having the amino acid sequence in which one amino acid or two or more amino acids are added to the amino acid sequence represented by SEQ ID NO: 2, and the amino acid sequence in which one amino acid or two or more amino acids in the amino acid sequence represented by SEQ ID NO: 2 are substituted by another amino acid or other amino acids. Further, in these recombinant human LH-RH receptor proteins, N-terminal signal peptides may be cleaved, side chains of amino acids in molecules may be protected with appropriate protective groups (for example, $C_{1-6}$ acyl groups such as formyl and acetyl), or sugar chains may be bound to the proteins.

Recombinant human LH-RH receptor proteins of the present invention may be different from the known human LH-RH receptor proteins such as natural human LH-RH receptor protein, a recombinant human LH-RH receptor protein produced by cultivating COS-7 cells containg a DNA coding for human LH-RH receptor protein, in the kind, size and/or numbers of the glycosyl chains. Thus, the molecular weight of the recombinant human LH-RH receptor protein may be different from the molecular weight of the known human LH-RH receptor proteins.

As the salts of the recombinant human LH-RH receptor proteins of the present invention, pharmaceutically acceptable acid addition salts are preferred among others. Examples of such salts include salts with inorganic acids (such as hydrochloric acid, phosphoric acid, hydrobromic acid and sulfuric acid) and salts with organic acids (such as acetic acid, formic acid, propiohic acid, fumaric acid, maleic acid, succinic acid, tartaric acid, citric acid, malic acid, oxalic acid, benzoic acid, methanesulfonic acid and benzenesulfonic acid).

The recombinant human LH-RH receptor protein of the present invention can be produced, for example, by cultivating the CHO cell of the present invention containing the vector bearing the DNA coding for the human LH-RH receptor protein, under such conditions that the DNA coding for the human LH-RH receptor protein can be expressed. The recombinant human LH-RH receptor protein can be isolated from the resulting cell containing the recombinant human LH-RH receptor protein, for example, according to the following methods.

When the recombinant human LH-RH receptor protein is extracted from the cells, the cells are collected by known methods after cultivation, and suspended in an appropriate buffer solution. Then, the cells are disrupted by supersonic waves, a homogenizer or freeze-thawing, followed by centrifugation or filtration to obtain a crude extract of the recombinant human LH-RH receptor protein.

The buffer solution may contain a protease inhibitor such as PMSF, pepstatin or leupeptin, and/or a detergent such as CHAPS, digitonin or Triton X-100 (registered trade mark, hereinafter occasionally abbreviated as "TM"). The recombinant human LH-RH receptor protein contained in the resulting extract can be purified by suitable combinations of the separating-purifying methods well known in the art. These known separating-purifying methods include methods utilizing a difference in solubility such as salting-out and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange chromatography, methods utilizing specific affinity such as affinity chromatography, methods utilizing a difference in hydrophobicity such as reverse phase high performance liquid chromatography, and methods utilizing a difference in isoelectric point such as isoelectric point electrophoresis.

When the recombinant human LH-RH receptor proteins thus obtained are free forms, they can be converted to appropriate salts by known methods or methods based thereon. Conversely, when the proteins are obtained in the salt state, they can be converted to the free forms or other salts by known methods or methods based thereon.

Before or after purification, the recombinant human LH-RH receptor protein can be modified with an appropriate protein modifying enzyme to arbitrarily modify the protein or to partially eliminate a polypeptide therefrom. The protein modifying enzymes used include trypsin, chymotrypsin, arginyl endopeptidase, protein kinase and glucosidase.

The recombinant human LH-RH receptor protein produced by cultivating the CHO cell containing the vector bearing the DNA coding for the human LH-RH receptor protein, under the conditions that the DNA coding for the human LH-RH receptor protein can be expressed, as described above, has activities substantially equivalent to those of the natural human LH-RH receptor protein. The substantially equivalent activities include, for example, ligand binding activity and signal information transmission. The ligand binding activity includes binding activity with, for example, LH-RH receptor agonist (e.g. LH-RH), LH-RH receptor superagonist (e.g. leuprorelin, leuprorelin acetate) or LH-RH receptor antagonist. As used herein, the "recombinant human LH-RH receptor protein" is a protein, mutein or peptide fragment having biological activities substantially equivalent to those of the natural human LH-RH receptor protein. Substantially equivalence will depend on the particular activity one is looking at. Biological activities include, for example, ligand binding and signal information transmission, such as activities enhancing or inhibiting arachidonic acid release, acetylcholine release, fluctuation in intracellular $Ca^{2+}$ concentration, generation of intracellular cAMP, generation of intracellular cGMP, production of inositol phosphate, fluctuation in cell membrane potential, phosphorylation of intracellular proteins, activation of c-fos, a reduction in pH, chemotactic activity, activation of G proteins and cell growth. The ligand binding activity includes binding with, for example, LH-RH receptor agonist (e.g. LH-RH), LH-RH receptors superagonist (e.g. leuprorelin, leuprorelin acetate) or LH-RH receptor antagonist. Preferably, the recombinant human LH-RH receptor protein will have at least two of these activities, most preferably at least three. In addition, the recombinant receptor protein will have at least 50% of the activity of the natural human LH-RH receptor protein, preferably at least 70%, most preferably at least 90%. Accordingly, quantitative factors such as the molecular weight of the receptor protein may be different.

As the peptide fragments of the recombinant human LH-RH receptor proteins of the present invention, for example, a site exposed outside the cell membranes is used. Specifically, the peptide fragment is analyzed to be an extracellular region (hydrophilic sites) by hydrophobic blot analysis. The peptide fragments may include hydrophobic sites. Furthermore, although peptides separately containing an individual domain can be used, peptides each containing a plurality of domains may be used As the salts of the peptide fragments of the recombinant human LH-RH receptor proteins of the present invention, pharmaceutically acceptable acid addition salts are preferred among others. Examples of such salts include salts with inorganic acids (such as hydrochloric acid, phosphoric acid, hydrobromic acid and sulfuric acid) and salts with organic acids (such as acetic acid, formic acid, propionic acid, fumaric acid, maleic acid, succinic acid, tartaric acid, citric acid, malic acid, oxalic acid, benzoic acid, methanesulfonic acid and benzenesulfonic acid).

The peptide fragments of the recombinant human LH-RH receptor proteins of the present invention or a salt thereof can be produced by peptide synthesis well known in the art or by cleaving the recombinant human LH-RH receptor proteins of the present invention with appropriate peptidases. For example, either solid phase synthesis methods or liquid phase synthesis methods may be employed for synthesis of the peptides. Namely, the target peptides can be produced by condensing peptide fragment(s) or amino acid (s) which can constitute the proteins of the present invention with residual moieties, and eliminating protective groups when the products have the protective groups. Known condensing methods and elimination of the protective groups include, for example, methods described in (1) to (5) given below:

(1) M. Bodansky and M. A. Ondetti, *Peptide Synthesis*, Interscience Publishers, New York (1966);

(2) Schroeder and Luebke, *The Peptide*, Academic Press, New York (1965);

(3) N. Izumiya et al., *Peptide Gosei no Kiso to Jikken (Fundamentals and Experiments of Peptide Synthesis)*, Maruzen (1985);

(4) H. Yazima, S. Sakakibara et al., *Seikagaku Jikken Koza (Course of Biochemical Experiments)*, 1, Chemistry of Proteins IV, 205 (1977); and (5) *Zoku Iyakuhin no Kaihatu (Development of Drugs, Second Series)*, 14, Peptide Synthesis, supervised by H. Yazima, Hirokawa Shoten.

After reaction, the peptide fragments of the present invention can be isolated by combinations of usual purifying methods such as solvent extraction, distillation, column chromatography, liquid chromatography and recrystallization. When the peptide fragments obtained by the above-mentioned methods are free forms, they can be converted to appropriate salts by known methods. Conversely, when the proteins are obtained in the salt state, they can be converted to the free forms by known methods.

The CHO cells containing the recombinant human LH-RH receptor proteins or the cell membrane fractions thereof, or the recombinant human LH-RH receptor proteins, the peptide fragments thereof or a salt thereof according to the present invention is useful for screening a compound or a salt thereof which has affinity for the LH-RH receptor, preferably human LH-RH receptor.

The compounds which have affinity for LH-RH receptors include following compounds:

(I) LH-RH receptor agonistic compounds:

The compounds have activities which stimulates release of LH and/or FSH by binding to an LH-RH receptor, which are sometimes called an LH-RH receptor agonist.

(II) LH-RH receptor superagonistic compounds:

The compounds have activities which stimulates release of excess LH and/or FSH by binding to an LH-RH receptor, which are sometimes called an LH-RH receptor superagonist.

(III) LH-RH receptor antagonistic compounds:

The compounds bind to an LH-RH receptor but have no activities which stimulates release of LH and/or FSH, which are sometimes called an LH-RH receptor antagonist.

Namely, the present invention provides:

(1) The method for screening a compound or a salt thereof which has affinity for an LH-RH receptor, which comprises comparing both following cases (i) and (ii),
(i) contacting the recombinant human LH-RH receptor protein, a peptide fragment thereof or a salt thereof of the present invention with a ligand to an LH-RH receptor, and
(ii) contacting the recombinant human LH-RH receptor protein, a peptide fragment thereof or a salt thereof of the present invention with a ligand to an LH-RH receptor and a test compound; and (2) The method for screening a compound or a salt thereof which has affinity for an LH-RH receptor, which comprises comparing both following cases (i) and (ii),
(i) contacting a ligand to an LH-RH receptor with the CHO cell or the cell membrane fraction thereof containing the recombinant human LH-RH receptor protein, and
(ii) contacting a ligand to an LH-RH receptor and a test compound with the CHO cell or the cell membrane fraction thereof containing the recombinant human LH-RH receptor protein.

Specifically, the screening method of the present invention comprises measuring the binding of a ligand to an LH-RH receptor to the recombinant human LH-RH receptor protein, the peptide fragment thereof or a salt thereof, or the CHO cell containing the recombinant human LH-RH receptor protein or the cell membrane fraction thereof, for both the cases of (i) and (ii), or measuring cell stimulation activities, followed by comparison.

More specifically, the present invention provides:

(1a) A method for screening a compound or a salt thereof which has affinity for an LH-RH receptor, which comprises comparing the binding amounts of both following cases (i) and (ii),
(i) contacting the recombinant human LH-RH receptor protein, a peptide fragment thereof or a salt thereof of the present invention with a labeled ligand to an LH-RH receptor, and
(ii) contacting the recombinant human LH-RH receptor protein, a peptide fragment thereof or a salt thereof of the present invention with a labeled ligand to an LH-RH receptor and a test compound;

(2a) A method for screening a compound or a salt thereof which has affinity for an LH-RH receptor, which comprises comparing the binding amounts of both following cases (i) and (ii),
(i) contacting the CHO cells or membrane fractions thereof containing a recombinant human LH-RH receptor protein of the present invention with a labeled ligand to an LH-RH receptor, and
(ii) contacting the CHO cells or membrane fractions thereof containing a recombinant human LH-RH receptor protein of the present invention with a labeled ligand to an LH-RH receptor and a test compound;

(2b) A method for screening a human LH-RH receptor agonistic compound or a salt thereof or a human LH-RH receptor superagonistic compound or a salt thereof, which comprises contacting the CHO cell or the cell membrane fraction thereof containing a recombinant human LH-RH receptor protein of the present invention with a test compound; and measuring Cell stimulation activities through the recombinant human LH-RH receptor (for example, activities enhancing or inhibiting arachidonic acid release, acetylcholine release, fluctuation in intracellular $Ca^{2+}$ concentration, generation of intracellular cAMP, generation of intracellular cGMP, production of inositol phosphate, fluctuation in cell membrane potential, phosphorylation of intracellular proteins, activation of c-fos, a reduction in pH, chemotactic activity, activation of G proteins and cell growth);

(2c) A method for screening a human LH-RH receptor antagonistic compound or a salt thereof which comprises comparing the activities of both following cases (i) and (ii),
(i) contacting the CHO cell or the cell membrane fraction thereof containing a recombinant human LH-RH receptor protein of the present invention with an LH-RH receptor agonist, and
(ii) contacting the CHO cell or the cell membrane fraction thereof containing a recombinant human LH-RH receptor protein of the present invention with an LH-RH receptor agonist and a test compound,
and in each case of (i) and (ii) measuring cell stimulation activities through the recombinant human LH-RH receptor (for example, activities enhancing or inhibiting arachidonic acid release, acetylcholine release, fluctuation in intracellular $Ca^{2+}$ concentration, generation of intracellular cAMP, generation of intracellular cGMP, production of inositol phosphate, fluctuation in cell membrane potential, phosphorylation of intracellular proteins, activation of c-fos, a reduction in pH, chemotactic activity, activation of G proteins and cell growth).

In the above-mentioned screening method (1a) or (2a), a compound which binds to the recombinant human LH-RH receptor protein or a peptide fragment thereof or the CHO cell or a membrane fraction thereof of the present invention inhibits the binding of a ligand to an LH-RH receptor with the recombinant human LH-RH receptor protein can be selected as the compound or a salt thereof which has affinity for an LH-RH receptor.

Further, in the above-mentioned screening method (2b), a compound which binds to the human LH-RH receptor protein to exhibit cell stimulation activities through the human LH-RH receptor (for example, activities enhancing or inhibiting arachidonic acid release, acetylcholine release, fluctuation in intracellular $Ca^{2+}$ concentration, generation of intracellular cAMP, generation of intracellular cGMP, production of inositol phosphate, fluctuation in cell membrane potential, phosphorylation of intracellular proteins, activation of c-fos, a reduction in pH, chemotactic activity, activation of G proteins and cell growth) can be selected as a human LH-RH receptor agonistic compound. Of the LH-RH receptor agonistic compounds, compounds which have extremely strong agonistic activity such as releasing excess LH and/or FSH can be selected as an LH-RH receptor superagonistic compound.

On the other hand, in the above-mentioned screening method (2c), of the test compounds, which has the activity of inhibiting the binding of an LH-RH receptor agonist to CHO cell or a membrane fraction thereof containing the recombinant human LH-RH receptor protein but does not have the cell stimulation activities can be selected as the human LH-RH receptor antagonistic compound.

Prior to the acquisition of the CHO cells containing the recombinant human LH-RH receptor proteins of the present invention, there were no animal cells capable of highly expressing the recombinant human LH-RH receptor proteins. It was therefore impossible to efficiently screen compounds or a salt thereof which have affinity for the LH-RH receptor, especially for the human LH-RH receptor. However, the CHO cells introduced by the human LH-RH receptor cDNA of the present invention can express the human LH-RH receptor proteins in large amounts, so that they are useful for the screening of the compounds which have affinity for the LH-RH receptor. In particular, the CHO cells capable of proliferation in suspension of the present invention are suitable for large-scale cultivation of the recombinant human LH-RH receptor proteins.

The screening methods of the present invention are explained concretely below.

When the CHO cells expressing the human LH-RH receptor proteins are used in the screening methods of the present invention, the CHO cells can be fixed with glutaraldehyde, formalin, etc. The fixation can be performed by methods well known in the art.

Ligands to the LH-RH receptor used in the screening methods of the present invention include known LH-RH receptor agonists such as LH-RH, LH-RH receptor superagonists such as leuroprelin, leuroprelin acetate, and LH-RH receptor antagonists.

As the labeled ligands to an LH-RH receptor, for example, the above described ligands labeled with [$^3$H], [$^{125}$I], [$^{14}$C] or [$^{35}$S] can be used. Specifically, LH-RH, leuroprelin, leuroprelin acetate labeled with [$^3$H], [$^{125}$I], [$^{14}$C] or [$^{35}$S] can be used. The labeled compounds can be produced by known methods, but LH-RH labeled with [$^{125}$I] or [$^3$H] (Amersham and Du Pondt) is available. Leuroprelin labeled with [$^{125}$I] can be produced according to Example 3 below.

Examples of the test compounds include peptides, proteins, non-peptide compounds, synthetic compounds, fermented products, cell extracts, plant extracts and animal tissue extracts, which may be either novel compounds or known compounds.

Specifically, when the above-mentioned screening method (1a) or (2a) is conducted, the CHO cell containing the recombinant human LH-RH receptor protein or the cell membrane fraction thereof, or the recombinant human LH-RH receptor protein or the peptide fragment thereof according to the present invention is first suspended in a buffer solution suitable for screening to prepare a receptor sample. Any buffer may be used as long as it does not inhibit the binding of LH-RH to the receptor. Examples thereof include phosphate buffer having a pH of about 6 to 8 and Tris-HCl buffer. Furthermore, for the purpose of reducing the non-specific binding, a detergent such as CHAPS, Tween 80 (TM) or digitonin can also be added. Furthermore, in order to inhibit the decomposition of ligand or the receptor due to a proteinase, a proteinase inhibitor such as PMSF, pepstatin or leupeptin, etc. can also be added. On the other hand, when the expression cell is an adhesive cell, LH-RH can be bound to the receptor, keeping the cell adhered to an incubator, namely with the cell grown.

In this case, Hanks' solution is used as a buffer. A certain amount (about 5,000 to about 1,000,000 cpm) of the labeled compound is added to about 0.01 to about 10 ml of the receptor expression cells or the receptor sample, and about $10^{-4}$ to $10^{-10}$ M of a test compound or the fermented product is allowed to coexist at the same time. On the other hand, in order to know the non-specific binding, a large excess of a non-labeled compound is also allowed to coexist to prepare another sample. The reaction is conducted at about 0° to 50° C. (preferably about 4° to 37° C.) for about 0.5 to 24 hours (preferably about 0.5 to 3 hours). After the reaction, the resulting product is filtered through a glass fiber filter and washed with an appropriate amount of the same buffer. Then, the amount of radiation remaining on glass fiber is measured with a gamma-ray counter or a scintillation counter. When the value obtained by subtracting the non-specific binding from the binding (total binding) in the state lacking the coexistent material is taken as 100%, a test compound depressing this value, for example, to 50% or less can be selected as a candidate compound which has affinity for an LH-RH receptor.

Further, when the above-mentioned screening method (2b) and (2c) are conducted, the cell stimulation activities through the recombinant human LH-RH receptor protein (for example, activities enhancing or inhibiting arachidonic acid release, acetylcholine release, fluctuation in intracellular $Ca^{2+}$ concentration, generation of intracellular cAMP, generation of intracellular cGMP, production of inositol phosphate, fluctuation in cell membrane potential, phosphorylation of intracellular proteins, activation of c-fos, a reduction in pH, chemotactic activity, activation of G proteins and secretion of hormones) and cell growth can be assayed by known methods or by use of commercial measuring kits. Specifically, the CHO cell containing the recombinant human LH-RH receptor protein is first cultivated on a multiwell plate. In conducting the screening, the medium is preliminarily replaced by a fresh medium or an appropriate buffer exhibiting no toxicity to the cell, and a test compound and the like are added thereto, followed by incubation for a definite period of time. Then, the cell is extracted or the supernatant is recovered, and the resulting product is determined according to each method. If the detection of the production of a substance (for example, arachidonic acid) used as an indicator for the cell stimulation activities is difficult because of a catabolic enzyme contained in the cell, an inhibitor to the catabolic enzyme may be added to conduct the assay. Further, activity such as inhibition of cAMP production can be detected as production inhibiting activity to the cell in which its basic production amount is increased by forskolin, etc.

The kit for screening of the present invention contains the CHO cell containing the recombinant human LH-RH receptor protein or the cell membrane fraction thereof, or the recombinant human LH-RH receptor protein, the peptide fragment thereof or a salt thereof according to the present invention.

Examples of the kits for screening of the present invention include the following:

(I) Kits for screening containing the CHO cell containing the recombinant human LH-RH receptor protein

[Reagents for Screening]

(1) Buffer A for Assay and Washing

Hanks' Balanced Salt Solution (Gibco) containing 0.2% bovine serum albumin (Sigma) and appropriate proteinase inhibitors (e.g. 0.25 mM PMSF, 1 µg/ml pepstatin, 20 µg/ml leupeptin, 100 µg/ml phosphoramidone)

The solution is sterilized through a filter having a pore size of 0.2 µm, and stored at 4° C., or may be prepared at the time of use.

(2) Recombinant Human LH-RH Receptor Protein Sample

A sample obtained by cultivation of CHO cells ($5 \times 10^4$ cells/well) expressing a recombinant human LH-RH receptor protein in a 24-well plate at 37° C. at 5% $CO_2$ and 95% air for 2 days.

(3) Labeled Ligand to an LH-RH Receptor

A solution of commercial ligand labeled with [$^3$H], [$^{125}$I], [$^{14}$C] or [$^{35}$S], for example, LH-RH, leuprelin, leuprelin acetate, is stored at −20° C. to −80° C., and diluted with a buffer for assay to a concentration of 25 nM.

(4) Ligand Standard Solution

Ligand to an LH-RH receptor such as LH-RH, leuprelin, leuprelin acetate is dissolved in PBS containing 0.1% bovine serum albumin (Sigma) to yield a concentration of 0.1 mM, and the solution is stored at −20° C.

[Assay]

(1) The CHO cells expressing the recombinant human LH-RH receptor proteins cultivated on the 24-well plate are washed once with 300 µl of the assay buffer A, followed by addition of 294 µl of the buffer to each well.

(2) After addition of 3 µl of a $10^{-3}$–$10^{-12}$M solution of a test compound, binding reaction is started at room temperature (about 1° to 30° C.) for 90 min by addition of 3 µl of 25 nM labeled ligand such as LH-RH, leuprelin, leuprelin acetate is added thereto. In order to know the non-specific binding, 3 µl of $10^{-4}$M non-labeled ligand such as LH-RH, leuprelin, leuprelin acetate is added in place of the test compound.

(3) The reaction solution is removed, and the plate is washed three times with 300 µl of the assay buffer A. The labeled ligand bound to the cells is recovered with 0.5 ml of 1N NaOH.

(4) When the radioactive ligand is labeled with [$^{125}$I], the radioactivity can be directly measured with a gamma-ray counter without mixing with the liquid scintillator.

In other cases, the recovered solution is mixed with appropriate volume of liquid scintillator A (Wako Pure Chemical Industries). The radioactivity is measured by use of a scintillation counter (Beckmann). The percent of the maximum binding (PMB) is calculated from the following equation.

$$PMB = (B-NSB)/(TB-NSB) \times 100(\%)$$

PMB: Percent of the maximum binding

B: Radioactivity when the test compound is added

NSB: Radioactivity when excessive (about $10^{-6}$M) cold ligand is added (Non-specific binding)

TB: Radioactivity when no test compound is added (Total binding)

(II) Kits for screening containing the CHO cell membrane fraction

[Reagents for Screening]

(1) Buffer B for Assay and Washing 25 mM Tris-HCl buffer (pH 7.4) containing 1 mM EDTA, 0.1% bovine serum albumin (Sigma) and appropriate proteinase inhibitors (eg. 0.25 mM PMSF, 1 µg/ml pepstatin, 20 µg/ml leupeptin, 100 µg/ml phosphoramidone)

The solution is stored at 4° C., or may be prepared at the time of use.

(2) Recombinant Human LH-RH Receptor Protein Sample

A sample is membrane fraction of CHO cells expressing human LH-RH receptor protein. Samples can be prepared from the CHO cells described above and stored at −80° C. prior to use.

(3) Labeled Ligand to an LH-RH Receptor

A solution of commercial ligand labeled with [$^3$H], [$^{125}$I], [$^{14}$C] or [$^{35}$S], for example, LH-RH, leuprelin, leuprelin acetate, is stored at −20° C. to −80° C., and diluted with a buffer for assay to a concentration of 3.6 nM.

(4) Ligand Standard Solution

Ligand to an LH-RH receptor such as LH-RH, leuprelin, leuprelin acetate is dissolved in PBS containing 0.1% bovine serum albumin (Sigma) to yield a concentration of 0.1 mM, and the solution is stored at −20° C. to −80° C.

[Assay]

(1) The membrane fraction of CHO cells expressing human LH-RH receptor protein is diluted to an appropriate concentration (about 0.1 to 5000 µg/ml, preferably about 1 to 500 µg/ml), and dispensed each 188 µl for a reaction.

(2) After addition of 2 µl of a $10^{-3-10-12}$M solution of a test compound, binding reaction is started at room temperature (about 1° to 30° C.) for 1 hour by addition of 10 µl of 3.6 nM labeled ligand such as LH-RH, leuprelin, leuprelin acetate. In order to know the non-specific binding, 2 µl of $10^{-4}$M non-labeled ligand such as LH-RH, leuprelin, leuprelin acetate is added in place of the test compound.

(3) The reaction solution is filtered through glass filter (Whatman GF/F), and is washed two times with 1 to 5 ml of the assay buffer B.

(4) When a radioactive ligand is labeled with [$^{125}$I], the labeled ligand remained on the filter can be directly measured with a gamma-ray counter without mixing with the liquid scintillator.

In other cases, appropriate volume of liquid scintillator A (Wako Pure Chemical Industries) is added to the filter, then the radioactivity is measured by use of a scintillation counter (Beckmann). The percent of the maximum binding (PMB) is calculated from the following equation.

$PMB=(B-NSB)/(TB-NSB)\times100(\%)$

PMB, B, NSB and TB have the same meanings as above.

The compounds or a salt thereof which have affinity for an LH-RH receptor obtained by the methods for screening or the kits for screening of the present invention are compounds inhibiting the binding of LH-RH to the recombinant human LH-RH receptor proteins of the present invention. The compounds are selected from test compounds such as peptides, proteins, non-peptide compounds, synthetic compounds, cell extracts, plant extracts and animal tissue extracts which may be novel or known. The compounds include compounds having cell stimulation activities through the human LH-RH receptors, or a salt thereof (so-called human LH-RH receptor agonistic compounds), or compounds having excess cell stimulation activities through the human LH-RH receptors, or a salt thereof (so-called human LH-RH receptor superagonistic compounds) and compounds having no cell stimulation activities or salts thereof (so-called human LH-RH receptor antagonistic compounds).

Compounds which have affinity for an LH-RH receptor obtained in the present invention include modified compounds such as chemical modification, substitution or designing of the obtained ones.

As the salts of the compounds which have affinity for an LH-RH receptor, biologically acceptable acid addition salts are preferred among others. Examples of such salts include salts with inorganic acids (such as hydrochloric acid, phosphoric acid, hydrobromic acid and sulfuric acid) and salts with organic acids (such as acetic acid, formic acid, propionic acid, fumaric acid, maleic acid, succinic acid, tartaric acid, citric acid, malic acid, oxalic acid, benzoic acid, methanesulfonic acid and benzenesulfonic acid).

Of the compounds which have affinity for an LH-RH receptor obtained by the methods for screening or the kits for screening of the present invention, LH-RH receptor agonistic compounds or a salt thereof are safe and non-toxic and are useful as pregnancy controlling composition or menses cycle controlling composition for animals such as rats, mice, chickens, rabbits, sheep, porcin, bovine, cats, dogs, monkeys, sacred baboons and chimpanzees, especially bovine. Specifically, they are useful as a fertility composition or a prophylactic and/or a therapeutic composition for breeding difficulties of animals.

The human LH-RH receptor superagonistic and antagonistic compounds obtained by the methods for screening or the kits for screening of the present invention are safe and non-toxic and useful as a prophylactic and/or therapeutic composition for diseases depending on sex hormone such as prostate cancer, uterine cancer, breast cancer, a pituitary tumor, prostatic hypertrophy, endometriosis, hysteromyoma or precocious puberty. They are also useful as a pregnancy controlling composition such as contraceptive or a menstrual cycle controlling composition.

The compounds or a salt thereof which have affinity for an LH-RH receptor obtained by the methods for screening or the kits for screening of the present invention can bind an LH-RH receptor and therefore they are also useful as a recomposition to detect or assay a receptor expression cell, LH-RH receptor protein in a body.

When the compounds or a salt thereof which have affinity for an LH-RH receptor obtained by the methods for screening or the kits for screening of the present invention are used as the above-mentioned pharmaceutical compositions, they can be formulated according to methods known in the art. For example, they can be given orally as tablets coated with sugar if necessary, capsules, elixirs and microcapsules, or parenterally in the form of injections such as sterile solutions or suspensions with water or with pharmaceutically acceptable solutions other than water. For example, the compounds or a salt thereof can be mixed with carriers, flavoring agents, excipients, vehicles, preservatives, stabilizing agents, binders, etc. in the form of unit dosage required for generally admitted pharmaceutical practice to prepare preparations. The amount of active ingredients in these preparations is adjusted so as to obtain appropriate doses within specified ranges.

Additives which can be mixed with tablets, capsules, etc. include, for example, binders such as gelatin, corn starch, tragacanth and gum arabic; excipients such as crystalline cellulose; swelling compositions such as corn starch, gelatin and alginic acid; lubricants such as magnesium stearate; sweeteners such as sucrose, lactose and saccharine; and flavoring compositions such as peppermint, acamono oil and cherry. When the preparation unit is in the capsule form, liquid carriers such as fat and oil may further be added to materials of the above-mentioned types. Sterile compositions for injection can be formulated according to usual pharmaceutical practice such as dissolution or suspension of active substances and naturally occurring vegetable oils such as sesame oil and coconut oil in vehicles such as water for injection.

Aqueous solutions for injection include, for example, physiological saline and isotonic solutions containing glucose or other adjuvants (for example, D-sorbitol, D-mannitol and sodium chloride), and may be used in combination with appropriate solubilizing adjuvants such as alcohols (for example, ethanol), polyalcohols (for example, polypropylene glycol and polyethylene glycol) and nonionic surface active compositions (for example, Polysolvate 80 (TM) and HCO-50). Oily solutions include sesame oil and soybean oil, and may be used in combination with solubilizing adjuvants such as benzyl benzoate, benzyl alcohol, etc. The preparations may further contain buffers (for example, phosphate buffer and sodium acetate buffer), soothing compositions (for example, benzalkonium chloride and procaine hydrochloride), stabilizing compositions (for example, human serum albumin and polyethylene glycol), preservatives (for example, benzyl alcohol and phenol), antioxidants, etc. The injections thus prepared are usually filled into appropriate ampuls. The preparations thus obtained are safe and low in toxicity, so that they can be given, for example, to warm-blooded animals (for example, rats, mice, chickens, rabbits, sheep, pigs, bovine, cats, dogs, monkeys, sacred baboons and humans, especially humans).

Although the dosage of the compounds or a salt thereof which have affinity for an LH-RH receptor varies depending upon the symptom, the oral dosage is generally about 0.1 to 100 mg per day, preferably about 1.0 to 50 mg, and more preferably about 1.0 to 20 mg, for adults (taken as 60 kg). When the preparations are parenterally given, the dosage varies depending upon the object to which the preparations are given, the organ to which they are given, the symptom, the route of administration, etc. For example, when the preparations are given in the injection form, it is advantageous that they are intravenously injected in a dosage of about 0.01 to 30 mg per day, preferably about 0.1 to 20 mg, and more preferably about 0.1 to 10 mg, for adults (taken as about 60 kg). For other animals, they can be given in terms of a dosage per about 60 kg.

When the compounds which have affinity for an LH-RH receptor are LH-RH receptor superagonistic compounds, reduction the concentration at which superagonistic activities such as excess LH or FSH release is shown to $1/1000$ to $1/10000$ by dilution make them LH-RH receptor agonists.

The CHO cells of the present invention wherein said cell is capable of continued production of the human LH-RH receptor proteins are cells capable of highly expressing the human LH-RH receptor proteins. In particular, the cells adapted to the CHO cells capable of proliferation in suspension are suitable for large-scale cultivation of the human LH-RH receptor proteins.

Furthermore, by screening compounds which have affinity for an LH-RH receptor using the CHO cells having ability to continue producing the human LH-RH receptor proteins or the cell membrane fractions thereof, or the recombinant human LH-RH receptor proteins or the peptide fragments thereof according to the present invention, the LH-RH receptor agonistic, superagonistic or antagonistic compounds can be advantageously selected. Accordingly, prophylactic or therpeutic compositions, for example, for prostate cancer, uterine cancer, breast cancer, a pituitary tumor, prostatic hypertrophy, endometriosis, hysteromyoma or precocious puberty. A pregnancy controlling composition such as contraceptive, ovulation-inhibiting composition, ovulation-inducing composition or a menstrual cycle controlling composition can also be provided.

When nucleotides, amino acids and so on are designated abbreviations in the specification and drawings, the abbreviations adopted by the IUPAC-IUB Commission on Biochemical Nomenclature or commonly used in the art are employed. For example, the following abbreviations are used. When the amino acids are capable of existing as optical isomers, it is understood that the L-forms are represented unless otherwise specified.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetraacetic acid
SDS: Sodium dodecyl sulfate
EIA: Enzyme immunoassay
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine
BSA: Bovine serum albumin Transformant *Escherichia coli* MV1184//pA1-11/hLH-RHR bearing plasmid pA1-11/hLH-RHR obtained in Example 1 given below was deposited with the National Institute of Bioscience and Human-technology (NIBH), the Agency of Industrial Science and Technology, the Ministry of International Trade and Industry, Japan, under the accession number FERM BP-4645 on Apr. 18, 1994 and deposited with Institution for Fermentation, Osaka, Japan (IFO) under the accession number IFO 15812 on Mar. 29, 1995.

CHO/L39-7 obtained in Example 2 given below was deposited with the National Institute of Bioscience and Human-technology (NIBH), the Agency of Industrial Science and Technology, the Ministry of International Trade and industry, Japan, under the accession number FERM BP-4953 on Dec. 22, 1994, and deposited with the Institute for Fermentation, Osaka, Japan (IFO) under the accession number IFO 50451 on Feb. 8, 1995.

CHO/LH-8 was deposited with the National Institute of Bioscience and Human-technology (NIBH), the Agency of Industrial Science and Technology, the Ministry of International Trade and Industry, Japan, under the accession number FERM BP-4973 on Jan. 19, 1995, and deposited with the Institute for Fermentation, Osaka, Japan (IFO) under the accession number IFO 50452 on Feb. 8, 1995.

SEQ NOs. in the Sequence listing are as follows:

[SEQ NO:1] Shows a nucleotide sequence of a cDNA coding for human LH-RH receptor protein.

[SEQ NO: 2] Shows an amino acid sequence of human LH-RH receptor protein.

[SEQ NO: 3] Shows a nucleotide sequence of a DNA oligomer for PCR which is used for a cloning of a cDNA coding for rat LH-RH receptor protein. This sequence is a partial nucleotide sequence of a cDNA coding for murine LH-RH receptor protein.

[SEQ NO: 4] Shows a nucleotide sequence of a DNA oligomer for PCR which is used for a cloning of a cDNA coding for rat LH-RH receptor protein. This sequence is a partial nucleotide sequence of a cDNA coding for murine LH-RH receptor protein.

[SEQ NO: 5] Shows a nucleotide sequence of a DNA oligomer for PCR which is used for a construction of human LH-RH receptor cDNA expression vector. This sequence contains a partial nucleotide sequence of a cDNA coding for human LH-RH receptor protein.

[SEQ NO: 6] Shows a nucleotide sequence of a DNA oligomer for PCR which is used for a construction of human LH-RH receptor cDNA expression vector. This sequence contains a partial nucleotide sequence of a cDNA coding for human LH-RH receptor protein.

EXAMPLES

The present invention will be described in more detail through the following reference examples and examples. It is understood of course that they are not intended to limit the scope of the invention. Genetic manipulation using *E. coli* was conducted according to the method described in Sambrook et al., *Molecular Cloning* Cold Spring Harbor Press, New York, 1989.

The $^1$H-NMR spectrum was measured with a Varian GEMINI 200 (200 MHz) type spectrometer using tetramethylsilane as an internal reference, and all δ values were shown by ppm.

Further, characters used in this specification have the following meanings:

s: singlet, d: doublet, t: triplet, dt: double triplet, m: multiplet, br: broad

[Reference Example 1]

Cloning of Rat LH-RH Receptor cDNA

Based on the nucleotide sequence of known mouse LH-RH receptor cDNA [J. Reinhort et al., *J. Biol. Chem.*, 267, 21281–21284 (1992) and M. Tatsunami et al. *Mol. Endocrinol.* 6, 1163–1169 (1992)], DNA oligomers (1) and (2) were synthesized. DNA oligomer (1) has a nucleotide sequence indicated by 5'-TGAAGCCTGTCCTTGGAGAAATATGGC-3' (SEQ ID NO:3 in the sequence listing) and has a sense sequence of −22 to +5 (a translation initiation site is taken as +1). DNA oligomer (2) has a nucleotide sequence indicated by 5'-AAAGTTGTAGAAGGCCTGATGCCACCA-3' (SEQ ID NO: 4 in the sequence listing) and has an anti-sense sequence of +610 to +636.

RNA was prepared from the rat testes, and purified to obtain poly(A)$^+$ RNA (mRNA purification kit, Pharmacia). cDNA was synthesized from 5 µg of the poly(A)$^+$ RNA by use of a reverse transcriptase. The RNA was digested, followed by polymerase chain reaction (PCR) using the above-mentioned DNA oligomers and Taq polymerase. The reaction was conducted first at 94° C. for 5 minutes, then, at 94° C. for 1 minute, at 55° C. for 2 minutes and at 72° C. for 3 minutes as 1 cycle, repeating 30 cycles, and finally, at 72° C. for 15 minutes. After the reaction, a specifically amplified DNA fragment was purified, the ends thereof were made flush with T4 polymerase, and was inserted into the HincII site of a pUC119 vector (Takara) to obtain plasmid pTS846. The nucleotide sequence of the inserted rat LH-RH receptor cDNA was determined by a conventional method using [α,$^{-32}$P]dCTP (Amersham) to be identified as the reported nucleotide sequence of rat LH-RH receptor cDNA [U. B. Kaiser et al., *Biochem. Biophys. Res. Commun.*, 189, 1645–1652 (1992)]. Thus, the plasmid containing the rat LH-RH receptor cDNA fragment was obtained.

[Reference Example 2]

Cloning of Human LH-RH Receptor cDNA

*E. coli* Y1090 was infected with λ phage of the cDNA library (λgt11, Clontech) prepared from the human pituitaries, and then, about 1×10$^4$ clones thereof were inoculated on each soft agar plate. The plaque was transferred onto a nitrocellulose filter, and thereafter treated in turn with a denaturing solution (0.5M NaOH, 1.5M NaCl), a neutralizing solution [0.5M Tris-HCl (pH 7.0), 1.5M NaCl] and 3×SSC (20×SSC=3M NaCl, 0.3M sodium citrate). After air drying, it was treated at 80° C. for 2 hours to fix DNA to the filter. On the other hand, the rat LH-RH receptor cDNA fragment obtained in Reference Example 1 was cut out with BamHI/SphI, and was labeled with [α-$^{32}$P]dCTP (Amersham DNA labeling kit) and was used as a probe. The filter to which the DNA was fixed was hybridized at 42° C. in a hybridization buffer [5×SSPE (20×SSPE=3M NaCl, 0.2M NaH$_2$PO$_4$ (pH 7.4), 20 mM EDTA), 10×Denhardt's solution, 50% formamide] containing the labeled probe. The filter was washed with 0.2×SSC and 0.1% SDS, followed by screening clones which hybridize to the probe by an autoradiogram. Phage DNA was extracted from clone λLRR29 obtained by this method, and cleaved with EcoRI to cut out a cDNA fragment, which was inserted into the EcoRI'site of a pUC118 vector to obtain plasmid pLRR29. The nucleotide sequence of the inserted portion was determined in the manner described above to be identified as the nucleotide sequence of human LH-RH receptor cDNA already reported [*Biochem. Biophys. Res. Commun.*, 189, 289–295 (1992)]. Thus, the plasmid containing the human LH-RH receptor cDNA was obtained.

[Reference Example 3]

Synthesis of Ethyl 2-Amino-5-phenylthiophene-3-carboxylate

Phenylacetaldehyde (50% diethyl phthalate solution; 12.05 g, 50 mmol) was added dropwise to a mixture of ethyl cyanoacetate (6.1 g, 50 mmol), sulfur (1.61 g, 50 mmol), triethylamine (3.5 ml, 25 mmol) and dimethylformamide (10 ml) with stirring at 45° C. for 20 minutes. After stirring the mixture at 45° C. for 9 hours, the resulting solution was concentrated to obtain a residue, which was extracted with ethyl acetate. The extract was washed with saline and dried on MgSO$_4$ and the solvent was distilled under reduced pressure. The residue was purified by silica gel column chromatography, and crystallized from ether-hexane to obtain slightly yellowish plate crystals (5.55 g, 45%).

Melting point: 124.5°–125.5° C. (literature value: 123°–124° C.)

Elemental analysis: As C$_{13}$H$_{13}$NO$_2$S

|  | C (%) | H (%) | N (%) |
|---|---|---|---|
| Calculated: | 63.13 | 5.30 | 5.66 |
| Found: | 62.99 | 5.05 | 5.63 |

$^1$H-NMR (200 MHz, CDCl$_3$) δ: 1.37 (3H, t, J=7.1 Hz), 4.30 (2H, d, J=7.1 Hz), 5.97 (2H, br), 7.17–7.46 (6H, m)

IR (KBr): 3448, 3320, 1667, 1590, 1549 cm$^{-1}$

[Reference Example 4]

Synthesis of Ethyl 2-Amino-4-methyl-5-(4-methoxyphenyl)thiophene-3-carboxylate

A mixture of 4-methoxyphenylacetone (16.5 g, 0.10 mol), ethyl cyanoacetate (12.2 g, 0.10 mol), ammonium acetate (1.55 g, 20 mmol), acetic acid (4.6 ml, 80 mmol) and benzene (20 ml) was refluxed by heating for 24 hours with removing generated water with a Dean and Stark apparatus. After cooling, the resulting solution was concentrated under reduced pressure to obtain a residue, which was distributed between dichloromethane and an aqueous solution of sodium bicarbonate. The organic layer was washed with saline and dried on MgSO$_4$, followed by removal of the solvent by distillation under reduced pressure. Sulfur (3.21 g, 0.10 mol) and diethylamine (10.4 ml, 0.10 mol) were added to a solution of the residue in ethanol (30 ml), and the mixture was stirred at 50° to 60° C. for 2 hours. Then, resulting solution was concentrated to obtain a residue, which was extracted with ethyl acetate. The extract was washed with saline and dried on MgSO$_4$, followed by removal of the solvent by distillation under reduced pressure. The residue was purified by silica gel column chromatography, and crystallized from ether-hexane to obtain pale yellow plate crystals (11.5 g, 40%).

Melting point: 79°–80° C.

Elemental analysis: As $C_{15}H_{17}NO_3S$

|  | C (%) | H (%) | N (%) | S (%) |
| --- | --- | --- | --- | --- |
| Calculated: | 61.83 | 5.88 | 4.81 | 11.01 |
| Found: | 61.81 | 5.75 | 4.74 | 10.82 |

$^1$H-NMR (200 MHz, CDCl$_3$) δ: 1.37 (3H, t, J=7.1 Hz), 2.28 (3H, s), 3.83 (3H, s), 4.31 (2H, q, J=7.1 Hz), 6.05 (2H, brs), 6.91 (2H, d, J=8.8 Hz), 7.27 (2H, d, J=8.8 Hz)

IR (KBr): 3426, 3328, 1651, 1586, 1550, 1505, 1485 cm$^{-1}$

FAB-MS m/z: 291 (M$^+$)

[Reference Example 5]

Synthesis of Ethyl 2-Amino-4-methyl-5-phenylthiophene-3-carboxylate

Colorless needle crystals (9.05 g, 40%) were obtained in the same manner as with Reference Example 4 with the exception that phenylacetone (11.6 g, 86.5 mmol) was substituted for 4-methoxyphenylacetone, and ethyl cyanoacetate (10.5 g, 86.5 mmol), ammonium acetate (1.34 g, 17.4 mmol), acetic acid (3.96 ml, 69.2 mmol), sulfur (2.78 g, 86.5 mmol) and diethylamine (8.95 ml, 86.5 mmol) were used.

Melting point: 64°–65° C. (recrystallized from ether-hexane, literature value: 95° C.)

Elemental analysis: As $C_{14}H_{15}NO_2S$

|  | C (%) | H (%) | N (%) |
| --- | --- | --- | --- |
| Calculated: | 64.34 | 5.79 | 5.36 |
| Found: | 64.51 | 5.77 | 5.29 |

$^1$H-NMR (200 MHz, CDCl$_3$) δ: 1.37 (3H, t, J=7.1 Hz), 2.33 (3H, s), 4.32 (2H, q, J=7.1 Hz), 6.09 (2H, br), 7.24–7.42 (5H, m)

IR (KBr): 3388, 3278, 1665, 1584, 1549, 1481 cm$^{-1}$

[Reference Example 6]

Diethyl {3-Ethoxycarbonyl-5-(4-methoxyphenyl)-4-methylthiophene-2-yl}aminomethylenemalonate Diethyl ethoxymethylenemalonate (7.45 g, 34.5 mmol) was added to the compound (10 g, 34.3 mmol) obtained in Reference Example 4, and the mixture was stirred at 120° C. for 2 hours. After cooling, ether was added to crystals precipitated from the resulting solution, and the crystals were collected by filtration. The crystals were washed again with ether, and dried on phosphorus pentaoxide under reduced pressure to obtain yellow crystals (14.2 g, 90%).

Melting point: 122°–123° C.

$^1$H-NMR (200 MHz, CDCl$_3$) δ: 1.32 (3H, t, J=7.1 Hz), 1.38 (3H, t, J=7.2 Hz), 1.41 (3H, t, J=7.2 Hz), 2.34 (3H, s), 3.85 (3H, s), 4.25 (2H, q, J=7.1 Hz), 4.38 (2H, q, J=7.2 Hz), 4.45 (2H, q, J=7.2 Hz), 6.95 (2H, d, J=8.8 Hz), 7.31 (2H, d, J=8.8 Hz), 8.22 (1H, d, J=13.4 Hz), 12.74 (1H, d, J=13.1 Hz)

IR (KBr): 2984, 1720, 1707, 1688, 1653, 1599, 1518, 1499 cm$^{-1}$

[Reference Example 7]

Diethyl {3-Carboxy-5-(4-methoxyphenyl)-4-methylthiophene-2-yl}aminomethylenemalonate A solution of potassium hydroxide (5.0 g, 75.7 mmol) in ethanol (30 ml) was added to a solution of the compound (7.0 g, 15.2 mmol) obtained in Reference Example 6 in dioxane (20 ml) with stirring at 60° to 70° C. After stirring at the same temperature for 1 hour, the solution was allowed to stand at room temperature for 1 hour. Then, 2-N hydrochloric acid (40 ml, 80 mmol) was added to the solution under ice cooling, and the resulting solution was concentrated under reduced pressure. The yellow residue collected by filtration was washed with cooled water-ethanol, and dried on phosphorus pentaoxide under reduced pressure to obtain a yellow powder (6.1 g, 93%).

Melting point: 184°–187° C.

$^1$H-NMR (200 MHz, DMSO-d$_6$) δ: 1.24 (3H, t, J=7.1 Hz), 1.28 (3H, t, J=7.2 Hz), 2.30 (3H, s), 3.80 (3H, s), 4.15 (2H, q, J=7.1 Hz), 4.24 (2H, q, J=7.2 Hz), 7.03 (2H, d, J=8.7 Hz), 7.37 (2H, d, J=8.7 Hz), 8.08 (1H, d, J=13.6 Hz), 12.41 (1H, d, J=13.6 Hz)

IR (KBr): 3422, 2980, 1719, 1653, 1607, 1551, 1512 cm$^{-1}$

[Reference Example 8]

Synthesis of Ethyl 4-Hydroxy-2-(4-methoxyphenyl)-3-methylthieno[2,3-b]pyridine-5-carboxylate The compound (6.0 g, 13.8 mmol) obtained in Reference Example 7 was added to polyphosphoric acid ester (PPE) (90 ml) little by little with stirring at 120° C. After stirring at the same temperature for 30 minutes, the resulting solution was poured on ice water and extracted with ethyl acetate. The extracts were collected and washed with saline. After drying on MgSO$_4$, the solvent was removed by distillation under reduced pressure. The resulting residue was purified by silica gel column chromatography to obtain a yellow powder (3.65 g, 77%). As a sample for element analysis, the resulting powder was recrystallized from ethanol to obtain yellow crystals.

Melting point: 162°–163° C.

Elemental analysis: As $C_{18}H_{17}NO_4S$

|  | C (%) | H (%) | N (%) | S (%) |
| --- | --- | --- | --- | --- |
| Calculated: | 62.96 | 4.99 | 4.08 | 9.34 |
| Found: | 62.89 | 5.04 | 4.01 | 9.34 |

$^1$H-NMR (200 MHz, CDCl$_3$) δ: 1.47 (3H, t, J=7.1 Hz), 2.63 (3H, s), 4.87 (3H, s), 4.49 (2H, q, J=7.1 Hz), 6.99 (2H, d, J=8.8 Hz), 7.44 (2H, d, J=8.8 Hz), 8.84 (1H, s), 2.11 (1H, s)

IR (KBr): 3434, 2992, 1692, 1601, 1582, 1535, 1504 cm$^{-1}$

FAB-MS m/z: 344 (MH$^+$)

[Reference Example 9]

Synthesis of Ethyl 4,7-Dihydro-7-(2-methoxybenzyl)-2-(4-methoxyphenyl)-3-methyl-4-oxothieno-[2,3-b]pyridine-5-carboxylate A solution of the compound (1.0 g, 2.91 mmol) obtained in Reference Example 8 in dimethylformamide (20 ml) was added dropwise to a suspension of sodium hydride (60% oily material, 123 mg, 3.08 mmol) in dimethylformamide (3 ml) in a stream of nitrogen under ice cooling. The resulting solution was stirred at room temperature for 23 hours and at 70° C. for 2 hours, and then, concentrated to obtain a residue, which was distributed between ethyl acetate and an aqueous solution of ammonium chloride. The aqueous layer was extracted with ethyl acetate. The extracts were collected and washed with saline. After drying on MgSO$_4$, the solvent was removed by distillation under reduced pressure. The resulting residue was purified by silica gel column chromatography to obtain a pale yellow amorphous powder (0.95 g, 70%). As a sample for element analysis, the resulting powder was recrystallized from dichloromethane-ether to obtain yellow columnar crystals.

Melting point: 165°–167° C.

Elemental analysis: As $C_{26}H_{25}NO_5 \cdot 0.5H_2O$

|  | C (%) | H (%) | N (%) |
|---|---|---|---|
| Calculated: | 66.08 | 5.55 | 2.96 |
| Found: | 66.33 | 5.44 | 2.74 |

$^1$H-NMR (200 MHz, CDCl$_3$) δ: 1.41 (3H, t, J=7.1 Hz), 2.65 (3H, s), 3.85 (3H, s), 3.86 (3H, s), 4.39 (2H, q, J=7.1 Hz), 5.16 (2H, s), 6.92–7.00 (4H, m), 7.21–7.41 (4H, m), 8.41 (1H, s)

IR (KBr): 2980, 1727, 1684, 1609, 1590, 1497, 1464 cm$^{-1}$

[Example 1]

Construction of Human LH-RH Receptor cDNA Expression Vector pA1-11 was used as an expression plasmid in CHO cells. pA1-11 was constructed in the following manner. A 1.4-kb DNA fragment containing a SRα promoter and polyadenylation signal was obtained from pTB1417 described in Japanese Patent Unexamined Publication (Laid-open) No. 5-076385 (EP-A2-491351) with HindIII and ClaI. Further, a 4.5-kb DNA fragment containing a dihydrofolate reductase (DHFR) gene was obtained from pTB348 [K. Naruo et al., Biochem. Biophys. Res. Commun., 128, 256–264 (1985)] with ClaI and SalI. The ends of these DNA fragments were made flush with T4 polymerase, and then, the fragments were ligated to each other with T4 DNA ligase to construct plasmid pAKK1-11 (pA1-11).

Then, based on the nucleotide sequence of the human LH-RH receptor cDNA obtained in Reference Example 2, DNA oligomers (3) and (4) were synthesized. DNA oligomer (3) has a nucleotide sequence indicated by 5'-GACGGCCGCAGATCTCCATGGCAAACAGTGCCTCTCC-3' (SEQ ID NO: 5 in the sequence listing) and containing a sense sequence of −1 to +20 (a translation initiation site is taken as +1) which has a restriction enzyme recognition site-containing anchor sequence at the 5'-terminus. DNA oligomer (4) has a nucleotide sequence indicated by 5'-GACAGATCTCACAGAGAAAAATATCCATAG-3' (SEQ ID NO: 6 in the sequence listing) and containing an anti-sense sequence of +966 to +987 which has a restriction enzyme recognition site-containing anchor sequence at the 5'-terminus. Using 1 ng of the above-mentioned pLRR29 plasmid as a template, PCR was conducted using the above-mentioned oligomers (3) and (4) and Taq polymerase under the same conditions as with Reference Example 1. After the reaction, the end of the specifically amplified DNA fragment was made flush using T4 polymerase, and the fragment was inserted into the HincII site of the pUC119 vector to obtain plasmid pLRR/PCR. The nucleotide sequence of the inserted fragment was determined in the same manner as described above. Then, the inserted fragment was cut out with SalI, and inserted into the SalI site of expression plasmid pA1-11 described above to obtain human LH-RH receptor cDNA expression plasmid pA1-11/hLH-RHR (FIG. 3). pA1-11/hLH-RH was introduced into E. coli MV1184 to obtain the transformant, E. coli MV1184//pA1-11/hLH-RHR.

[Example 2]

Expression of Human LH-RH Receptor cDNA in CHO (dhfr$^-$) Cells

In Ham F-12 medium containing 10% fetal calf serum in a dish of 10 cm-diameter, 1×10$^6$ CHO cells (dhfr$^-$) were cultivated for 24 hours, and 0.5 to 1 μg of human LH-RH receptor cDNA expression plasmid pA1-11/hLH-RHR obtained in Example 1 was introduced into the cells by the calcium phosphate method. The medium was changed with DMEM medium containing 10% dialyzed fetal calf serum, 24 hours after introduction, and cells which reserve the introduced gene in their chromosomes were selected. The selected cells were further cloned from the single cell by the limiting dilution method to obtain cell line CHO/L39 which stably expresses the human LH-RH receptor protein. This cell line was repeatedly cloned to obtain cell line CHO/L39-7 which expresses the receptor in higher amount. In this case, use of a medium containing MTX, a DHFR inhibitor, makes it possible to obtain a cell line in which an introduced gene is amplified and which expresses the desired protein with higher amount.

[Example 3]

Assay of Human LH-RH Receptor Activity

The LH-RH receptor protein activity of the CHO cells or the cell membrane fraction thereof was assayed by the following method:

(1) preparation of [$^{125}$I]leuprelin

10 μl of 0.3 mM leuprelin, 10 μl of 0.01 mg/ml lactoperoxidase, 10 μl of iodine 125 (37 MBq, Amersham, IMS30) and 10 μl of 0.001% H$_2$O$_2$ were mixed, followed by reaction at room temperature for 20 minutes. Then, 700 μl of 0.05% TFA was added to terminate the reaction, followed by separation by HPLC. A TSK gel ODS-80 (TM) CTR was used as the column, and the elution conditions were as shown in Table 1. The elution temperature was room temperature, and the elution speed was 1 ml/minute. Peak portions (26 to 27 minutes) of [$^{125}$I]leuprelin were fractionated, and the specific activity thereof was assayed with a gamma-ray counter.

TABLE 1

| Minute | Eluent | |
|---|---|---|
| 0–3 | 0.05% TFA | |
| 3–7 | 0.05% TFA | 0–20% CH$_3$CN |
| 7–40 | 0.05% TFA | 20–40% CH$_3$CN |
| 40–45 | 0.05% TFA | 40–70% CH$_3$CN |
| 45–50 | 0.05% TFA | 70% CH$_3$CN |

(2) Assay of LH-RH Receptor Activity of Cells

First, the human LH-RH receptor expression cells were cultivated on a 24-well plate. After washing once, binding reaction was conducted in 300 μl of buffer A for assay (Hanks' solution containing 0.2% BSA, 0.25 mM PMSF, 1 μg/ml pepstatin, 20 μg/ml leupeptin and 100 μg/ml phosphoramidone) supplemented with 250pM[$^{125}$I] leuprorelin as a ligand, for 90 minutes. After completion of the reaction, the supernatant was removed, followed by washing three times with 300 μl of the buffer for assay. After stripping of the cells with 1N NaOH, the amount of residual [$^{125}$I] was measured by a gamma-ray counter. The resulting value was taken as the total binding. Further, 1 μM unlabeled leuprorelin was added in the binding reaction, followed by a similar procedure. The amount of [$^{125}$I] obtained was taken as the non-specific binding. The value obtained by subtracting the non-specific binding from the total binding was taken as the specific binding. Results thereof are shown in Table 2.

TABLE 2

| Cell Line | Total Binding (cpm) | Non-specific Binding (cpm) | Specific Binding (cpm) |
|---|---|---|---|
| CHO/L39 | 17536 | 1446 | 16091 |
| CHO/L39-7 | 23420 | 1143 | 22268 |

[Example 4]

Preparation of CHO Cell Membrane Fraction Containing Human LH-RH Receptor

The human LH-RH receptor expression cells ($10^9$ cells) obtained in Example 2 were suspended in phosphate buffered saline containing 5 mM EDTA (PBS-EDTA), and centrifuged at 100×g for 5 minutes. To cell pellets, 10 ml of a cell homogenating buffer (10 mM NaHCO$_3$, 5 mM EDTA, pH 7.5) was added, followed by homogenization with a Polytron homogenizer. After centrifugation at 400×g for 15 minutes, the supernatant was placed in an ultracentrifugal tube, and centrifuged at 100,000×g for 1 hour to obtain a cell membrane fraction precipitate. This precipitate was suspended in 2 ml of an assay buffer, and centrifuged at 100,000×g for 1 hour. The cell membrane fraction recovered as a precipitate was suspended in 20 ml of the assay buffer again. The suspension was dispensed and stored at −80° C. It was defrosted at every time of use.

[Example 5]

Assay of [$^{125}$I]-Leuprorelin Binding Inhibition Ratio

The CHO cell membrane fraction prepared in Example 4 was diluted with an assay buffer B (25 mM Tris-HCl buffer (pH 7.4) containing 1 mM EDTA, 0.1% BSA, 0.25 mM PMSF, 1 µg/ml pepstatin, 20 µg/ml leupeptin and 100 µg/ml phosphoramidone) to yield 200 µg/ml, and 188 µl of the diluted suspension was poured into each tube. Then, 2 µl of a solution of 2 mM compound (compound produced in Reference Example 9, hereinafter the same) in 60% dimethyl sulfoxide (DMSO) and 10 µl of 3.6 nM [$^{125}$I]-leuprorelin were concurrently added thereto. In order to assay the maximum binding, a resulting solution containing 2 µl of 60% DMSO and 10 µl of 3.6 nM [$^{125}$I]-leuprorelin was prepared. Further, in order to assay the non-specific binding, a solution containing 2 µl of a solution of 100 µM leuprorelin in 60% DMSO and 10 µl of 3.6 nM [$^{125}$I]-leuprorelin was also prepared at the same time.

Using the human LH-RH receptor expression CHO cell membrane fraction, reaction was conducted at 25° C. for 60 minutes. After the reaction, the resulting solution was filtered with suction through a Whatman glass filter (GF-F) treated with polyethyleneimine. After the filtration, the radioactivity of [$^{125}$I]-leuprorelin left on the filter was measured with a gamma-ray counter.

The binding inhibition rate of each sample to be tested was determined according to the following equation:

$$\frac{(TB - SB)}{(TB - NSB)} \times 100 \, (\%)$$

wherein SB represents the radioactivity when the compound is added, TB represents the maximum binding radioactivity, and NSB represents the non-specific binding radioactivity. As a result, the compound produced in Reference Example 9 exhibited a binding inhibition activity of 67%, which proved that the compound was useful as a human LH-RH receptor antagonistic compound.

[Example 6]

Large-scale Culture in suspension of Human LH-RH Receptor Expression CHO Cells

Cell line CHO/L39-7 (2×10$^7$ cells) highly expressing the human LH-RH receptor protein obtained in Example 2 were cultivated in 100 ml of TE medium [a 1:1 (v/v) mixed medium of Daigo T medium (Nippon Seiyaku) containing insulin (5 mg/l), transferrin (10 mg/l), ethanolamine (1.53 mg/l) and sodium selenite (0.0043 mg/l) and E-RDF medium (Kyokuto Seiyaku)] supplemented with 1% dialyzed fetal calf serum in a 125-ml Techne spinner flask at an agitation speed of 50 rpm. This procedure was repeated further three times, thereby obtaining cell line CHO/LS which is adaptated to proliferation in suspension. Cell line CHO/LS (5×10$^7$ cells) thus obtained were suspended in the above-mentioned medium (500 ml), and placed in a 500-ml Techne spinner flask. Then, the cells were cultivated with stirring at a speed of 50 rpm at 37° C. for 4 days. Cells proliferated were collected by centrifugation, transferred to the above-mentioned medium (3 liters), placed in a 3-liter Techne spinner flask, and cultivated until the late logarithmic growth phase. The cells were transplanted to a 50-liter fermentor containing the above-mentioned medium (25 liters) at an inoculation density of 7×10$^4$ cells/ml, and cultivated at an agitation speed of 30 rpm at 37° C. for 3 days to obtain 7×10$^9$ cells of CHO/LS. From this cell line (5×10$^8$ cells), a membrane fraction (69 mg) was produced in the same manner as with Example 4. The human LH-RH receptor activity per 80 µg of the membrane fraction was measured in the same manner as with Example 3. Results thereof are shown in Table 3.

TABLE 3

| Total Binding (cpm) | Non-specific Binding (cpm) | Specific Binding (cpm) |
|---|---|---|
| 11905 | 1983 | 9922 |

[Example 7]

Assay of Intercellular Second Messenger of Human LH-RH Receptor Expression CHO Cells Changes in intercellular calcium concentration were examined by use of a specific fluorescent material (fura-2). The human LH-RH receptor expression CHO cells were cultivated on a 6-cm dish tiled with cover glass for 3 days. The cells were washed three times with a calcium assay buffer (Hanks' solution containing 0.1% BSA), and 2.5 ml of the same buffer containing 4 µM fura-2 was added thereto, followed by standing at room temperature for 90 minutes. After washing three times with the buffer, the cover glass was transferred to a cuvette, and the assay was conducted with a fluorescence spectrophotometer (FIG. 4).

The concentration of inositol phosphate ($IP_s$) was measured by labeling the cells with [$^3H$] inositol. The human LH-RH receptor expression CHO cells ($4\times10^4$ cells) were cultivated on a 24-well plate for 48 hours, and 2.5 µCi per well of myo [2-$^3H$] inositol (Amersham) was added thereto, followed by further cultivation for 24 hours. The cells were washed with an IP assay buffer [20 mM HEPES (pH 7.4), 140 mM NaCl, 4 mM KCl, 1 mM $NaH_2PO_4$, 1 mM $MgCl_2$, 1.25 mM $CaCl_2$, 10 mM LiCl, 10 mM glucose, 0.1% BSA], and the same buffer was added thereto, followed by standing at 37° C. for 30 minutes. The medium was changed with 500 µl of the same buffer, and LH-RH was added thereto, followed by reaction at 37° C. for 10 minutes. Then, 100 µl of 10% perchloric acid was added, and the mixture was allowed to stand at 0° C. for 30 minutes. Thereafter, 150 µl of 1.53M KOH and 75 mM HEPES was added thereto for neutralization. After further standing at 0° C. for 30 minutes, the product was centrifuged, and the supernatant was purified through an anion exchange column (AG1-X8). The column was washed with $H_2O$ and a washing solution (5 mM sodium tetraborate, 60 mM ammonium formate), and then, eluted with 1M formic acid and 0.1M ammonium formate. The radioactivity of the eluate was assayed with a liquid scintillation counter (LSC) (FIG. 5).

The concentration of arachidonic acid was measured by labeling the cells with [$^3H$] arachidonic acid. The human LH-RH receptor expression CHO cells ($4\times10^4$ cells) were cultivated on a 24-well plate for 48 hours, and 0.25 µCi per well of [5,6,8,9,11,12,14,15-$^3H$] arachidonic acid (Amersham) was added thereto, followed by further cultivation for 24 hours. The cells were washed with an arachidonic acid assay buffer [DMEM medium containing 20 mM HEPES (pH 7.4) and 0.2% BSA], and the same buffer was added thereto, followed by standing at 37° C. for 30 minutes. The medium was changed with 500 µl of the same buffer, and LH-RH was added thereto, followed by standing at 37° C. for 15 minutes. Then, the radioactivity of the supernatant was assayed with an LSC (FIG. 6).

Figure 6:
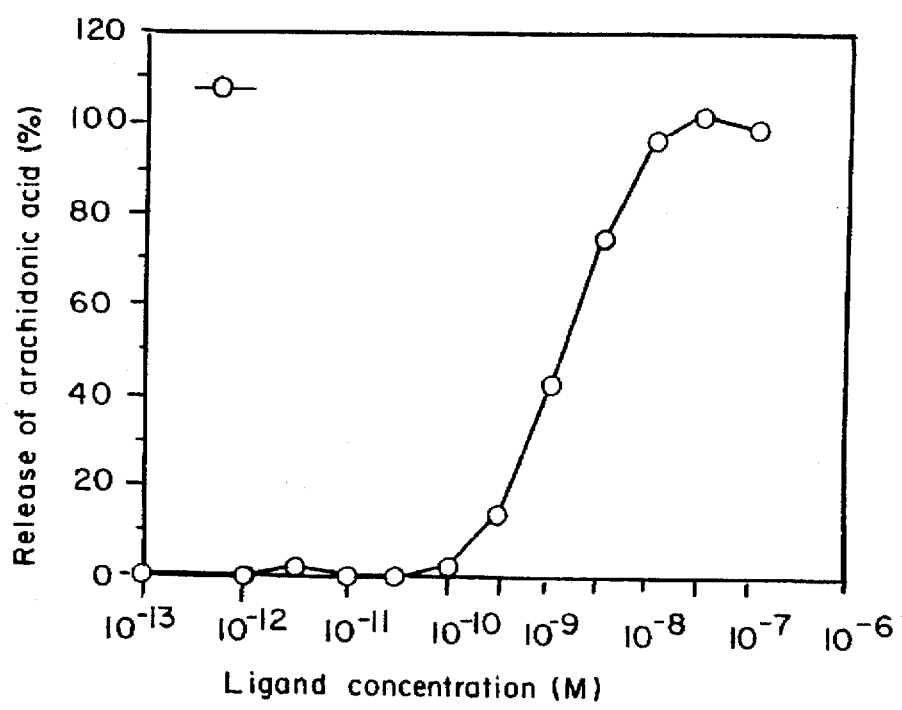
FIG. 6 is a graph showing changes in release of arachidonic acid concentration on stimulation of a CHO/L39-7 cell by LH-RH, wherein the numbers on the ordinate indicate the relative value(%) of the release of arachidonic acid concentration by stimulations of LH-RH at each concentration based on the release of arachidonic acid concentration (cpm, 100%) by the stimulation at $10^{-7}$ M LH-RH, and the numbers on the abscissa indicate the LH-RH concentration (log(LH-RH)).

As apparent from FIGS. 4, 5 and 6, for the CHO/L39-7 cells, the human LH-RH receptor expression CHO cells of the present invention, the production of $IP_s$ due to LH-RH stimulation, an increase of intracellular $Ca^{2+}$ subsequent thereto, and further the release of arachidonic acid were observed. Accordingly, intracellular signals demonstrated to be produced following the LH release in the pituitary cells were all observed. This reveals that the CHO/L39-7 cell line of the present invention is excellent an evaluation system for screening agonists/antagonists to LH-RH receptors or the assay of antagonist activity.

The invention has been described in detail with reference to the preferred embodiments thereof. However, it will be appreciated that those skilled in the art, upon consideration of this disclosure, may make modifications and improvements within the spirit and scope of the invention.

What is claimed is:

1. The CHO cell line CHO/L39-7 (FERM BP-4953).

2. The CHO cell line CHO/LH-8 (FERM BP-4973).

* * * * *